United States Patent
Meng

(10) Patent No.: US 8,579,885 B2
(45) Date of Patent: Nov. 12, 2013

(54) MEMS ELECTROCHEMICAL BELLOWS ACTUATOR

(75) Inventor: Ellis Meng, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 537 days.

(21) Appl. No.: 12/709,335

(22) Filed: Feb. 19, 2010

(65) Prior Publication Data

US 2010/0222769 A1  Sep. 2, 2010

Related U.S. Application Data

(60) Provisional application No. 61/154,327, filed on Feb. 20, 2009, provisional application No. 61/266,978, filed on Dec. 4, 2009, provisional application No. 61/266,977, filed on Dec. 4, 2009.

(51) Int. Cl.
*A61K 9/22*  (2006.01)

(52) U.S. Cl.
USPC ........................................... 604/891.1

(58) Field of Classification Search
USPC .................. 604/114, 118, 132, 133, 891.1
See application file for complete search history.

(56) References Cited

U.S. PATENT DOCUMENTS

| | | | |
|---|---|---|---|
| 2,497,906 A | 2/1950 | Peters et al. | |
| 4,699,615 A | 10/1987 | Fischell et al. | |
| 4,712,583 A | 12/1987 | Pelmulder et al. | |
| 4,919,167 A | 4/1990 | Manska | |
| 4,946,448 A | 8/1990 | Richmond | |
| 5,025,829 A | 6/1991 | Edwards et al. | |
| 5,090,963 A * | 2/1992 | Gross et al. | 604/132 |
| 5,135,499 A * | 8/1992 | Tafani et al. | 604/141 |
| 5,318,557 A | 6/1994 | Gross | |
| 5,472,122 A | 12/1995 | Appleby | |

(Continued)

FOREIGN PATENT DOCUMENTS

WO    2001066173 A1    9/2001

OTHER PUBLICATIONS

Office Action, dated Apr. 13, 2012, from U.S. Appl. No. 12/708,188, filed Feb. 19, 2010, entitled "Drug Delivery Device With In-Plan Bandpass Regulation Check Valve in Heat-Shrink Packaging," Ellis Meng and Ronalee Lo Mann, inventors, published Aug. 26, 2010 as US Publication No. 2009/0217209.

(Continued)

*Primary Examiner* — Theodore J Stigell
*Assistant Examiner* — Diva K Chander
(74) *Attorney, Agent, or Firm* — McDermott Will & Emery LLP

(57) ABSTRACT

An implantable fluid delivery system may include a fluid reservoir configured to hold a supply of fluid, dispense that fluid under the control of an actuator, and be implanted within the body of a living host. The actuator may include a bellows configured to expand in a direction when inflated. The bellows may have folds with surfaces which run substantially perpendicular to the direction of expansion in a collapsed state and which define a stacked set of convolutions. Each convolution may have a collapsed height of no more than 1 mm and a width perpendicular to the direction of expansion of no more than 8 mm. Electrodes may be configured to come in electrical contact with an electrolyte within the bellows and to cause electricity to run through the electrolyte, thereby causing the electrolyte to break down into a gas and, in turn, to cause the bellows to expand.

8 Claims, 20 Drawing Sheets

(56) References Cited

U.S. PATENT DOCUMENTS

| | | | |
|---|---|---|---|
| 5,771,935 A | 6/1998 | Myers | |
| 5,775,671 A | 7/1998 | Cote, Sr. | |
| 5,906,597 A | 5/1999 | McPhee | |
| 6,079,449 A | 6/2000 | Gerber | |
| 6,089,272 A | 7/2000 | Brand et al. | |
| 6,960,192 B1 | 11/2005 | Flaherty et al. | |
| 7,887,508 B2 * | 2/2011 | Meng et al. | 604/114 |
| 2001/0025160 A1 | 9/2001 | Felix et al. | |
| 2003/0229310 A1 | 12/2003 | Flaherty et al. | |
| 2004/0054333 A1 | 3/2004 | Theeuwes et al. | |
| 2004/0068224 A1* | 4/2004 | Couvillon et al. | 604/67 |
| 2005/0013805 A1 | 1/2005 | Tavori | |
| 2008/0039792 A1* | 2/2008 | Meng et al. | 604/114 |
| 2008/0086095 A1 | 4/2008 | Dikeman et al. | |
| 2008/0230053 A1 | 9/2008 | Kraft et al. | |
| 2008/0255500 A1 | 10/2008 | Kissinger et al. | |
| 2010/0217209 A1 | 8/2010 | Meng et al. | |

OTHER PUBLICATIONS

Bohm, S. et al. 2000. A closed-loop controlled electrochemically actuated micro-dosing system. Journal of Micromechanics and Microengineering, vol. 10, No. 4, 2000, pp. 498-504.

Feng, G.-H. et al. 2003. Universal concept for fabricating micron to millimeter sized 3-D parylene structures on rigid and flexible substrates, Technical Digest of the 16th IEEE International Conference on Micro Electro Mechanical Systems (MEMS 2003), Kyoto, Japan, Jan. 19-23, 2003, pp. 594-597.

Gensler, H. et al. 2010. Implantable MEMS Drug Delivery Devices for Cancer Radiation Reduction. MEMS 2010, Hong Kong, China, Jan. 24-28, 2010, pp. 23-26.

Kang, H.-W. et al. 2006. Development of a micro-bellows actuator using micro-stereolithography technology. Microelectronic Engineering, vol. 83, No. 4-9, 2006, pp. 1201-1204.

Li, P.-Y. et al. 2007. An Electrochemical Intraocular Drug Delivery Device. MEMS 2007, Kobe, Japan, Jan. 21-25, 2007 pp. 15-18.

Li, P.-Y. et al. 2007. Surgical Testing of a Microelectromechanical Systems (MEMS) Ocular Drug Delivery System. BMES Annual Fall Meeting, Los Angeles, California, USA, Sep. 26-29, 2007. Abstract only.

Li, P.-Y. et al. 2008. An Electrochemical Intraocular Drug Delivery Device. Sensors and Actuators A: Physical, vol. 143, Issue 1, 2008, pp. 41-48.

Li, P.-Y. et al. 2009. A Parylene Bellows Electrochemical Actuator for Intraocular Drug Delivery. Transducers 2009, Denver, Colorado, USA, Jun. 21-25, 2009, pp. 1461-1464.

Li, P.-Y. et al. 2010. A Parylene Bellows Electrochemical Actuator. IEEE/ASME Journal of Microelectromechanical Systems, vol. 19, No. 1, 2010, pp. 215-228.

Lo, R. et al. 2006. A Passive Refillable Intraocular MEMS Drug Delivery Device. IEEE Engineering in Medicine and Biology Society Special Topic Conference on Microtechnologies in Medicine and Biology, Okinawa, Japan, May 9-12, 2006, pp. 74-77.

Lo, R. et al. 2007. Refillable MEMS Drug Delivery Pump for Chronic Ocular Disease. ARVO 2007, Ft. Lauderdale, Florida, USA, May 6-10, 2007. Abstract only.

Lo, R. et al. 2008. A Refillable Microfabricated Drug Delivery Device for Treatment of Ocular Diseases. Lab on a Chip, vol. 8, Issue 7: pp. 1027-1030.

Lo, R. et al. 2008. In Vivo Studies Demonstrating Feasibility and Biocompatibility of a MEMS Ocular Drug Delivery System. BMES Annual Fall Meeting, St. Louis, Missouri, USA, Oct. 2-4, 2008. Abstract only.

Lo, R. et al. 2009. A Passive MEMS Drug Delivery Pump for Treatment of Ocular Diseases. Biomedical Microdevices, vol. 11, No. 5, 2009, pp. 959-970.

Luharuka, R. et al. 2004. Design, fabrication, and testing of a near constant pressure fuel delivery system for miniature fuel cells. Sensors and Actuators A: Physical, vol. 112, No. 2-3, 2004, pp. 187-195.

Meng, E. 2009. Implantable Microfluidic Delivery Platforms for Chronic Administration of Agents for Scientific Discovery and Therapy. AALAS National Meeting, Denver, Colorado, USA, Nov. 8-12, 2009. Abstract only.

Meng, E. 2009. Implantable Microfluidic Delivery Platforms for Chronic Administration of Agents for Scientific Discovery and Therapy. Illuminating the Genetic Architecture of Common Eye Disease, Avalon, California, USA, Feb. 3-7, 2009. Abstract only.

Meng, E. et al. 2000. A Check-Valved Silicone Diaphragm Pump. MEMS 2000, Miyazaki, Japan, Jan. 23-27, 2000, pp. 62-67.

Meng, E. et al. 2006. Electrolysis-driven Drug Delivery for Treatment of Ocular Disease. μTAS 2006, Tokyo, Japan, Nov. 5-9, 2006, pp. 633-635.

Meng, E. et al. 2008. Implantable MEMS Drug Delivery Systems for Administration of Unaltered Therapeutic Agents. USC Translational Nanoscience Conference: Re-Engineering Basic and Clinical Research to Catalyze Translational Nanoscience, Los Angeles, California, USA, Mar. 20-21, 2008. Abstract only.

Meng, E. et al. 2009. Implantable MEMS Drug Delivery Pumps for Small Animal Research. IEEE Engineering in Medicine and Biology Conference, Minneapolis, Minnesota, Sep. 2-6, 2009, pp. 6696-6698.

Metref, L. et al. 2007. Contactless Electrochemical Actuator for Microfluidic Dosing. IEEE/ASME Journal of Microelectromechanical Systems, vol. 16, No. 4, 2007, pp. 885-892.

Neagu, C. R. et al. 1996. An electrochemical microactuator: Principle and first results. IEEE/ASME Journal of Microelectromechanical Systems, vol. 5, No. 1, 1996, pp. 2-9.

O'Keefe, D. et al. 1994. Patient-controlled analgesia using a miniature electrochemically driven infusion pump. British Journal of Anaesthesia, vol. 73, No. 6, 1994, pp. 843-846.

Pang, C. et al. 2006. Electrolysis-based diaphragm actuators. Nanotechnology, vol. 17, No. 4, 2006, pp. S64-S68.

Saati, S. et al. 2007. Surgical Methods to Place a Novel Refillable Ocular Microelectromechanical System (MEMS) Drug Delivery Device. ARVO 2007, Ft. Lauderdale, Florida, USA, May 6-10, 2007. Abstract only.

Saati, S. et al. 2008. Surgical Methods to Place a Novel Refillable Ocular Microelectromechanical System (MEMS) Drug Delivery Device. ARVO 2008, Ft. Lauderdale, Florida, USA, Apr. 27-May 1, 2008. Abstract only.

Saati, S. et al. 2009. Mini Drug Pump for Ophthalmic Use. American Ophthalmological Society Annual Meeting, Half Moon Bay, California, USA, May 14-17, 2009. Abstract only.

Saati, S. et al. 2009. Mini Drug Pump for Ophthalmic Use. Transactions of the American Ophthalmological Society, vol. 107, 2009, pp. 60-71.

Saati, S. et al. 2010. Mini Drug Pump for Ophthalmic Use. Current Eye Research, vol. 35, No. 3, 2010, pp. 192-201.

Stanczyk, T. et al. 2000. A microfabricated electrochemical actuator for large displacements. IEEE/ASME Journal of Microelectromechanical Systems, vol. 9, No. 3, 2000, pp. 314-320.

Xie, J. et al. 2004. An electrochemical pumping system for on-chip gradient generation. Analytical Chemistry, vol. 76, No. 13, 2004, pp. 3756-3763.

Yang, X. et al. 1997. Micro bellow actuators, Proceedings of International Conference on Solid-State Sensors and Actuators (Transducers 97), Chicago, IL, USA, Jun. 16-19, 1997, pp. 45-48.

Yuan, G. et al. 2005. Kinematically-stabilized microbubble actuator arrays, Technical Digest of the 18th IEEE International Conference on Micro Electro Mechanical Systems (MEMS 2005), Miami, FL, USA, Jan. 30-Feb. 3, 2005, pp. 411-414.

Whalen, J. et al. 2005. Electrochemical Deposition of Platinum from Aqueous Ammonium Hexachloroplatinate Solution. Journal of the Electrochemical Society, vol. 152: pp. C738-C743.

Chen, P.-J. et al. 2006. Surface-Micromachined In-Channel Parylene Dual Valves for Unpowered Microflow Regulation. Hilton Head 2006: A Solid State Sensors, Actuators and Microsystems Workshop, Hilton Head Island, South Carolina, USA, Jun. 4-8, 2006, pp. 205-208.

(56) References Cited

OTHER PUBLICATIONS

Chen, P.-J. et al. 2007. Surface-Micromachined Parylene Dual Valves for On-Chip Unpowered Microflow Regulation. IEEE/ASME Journal of Microelectromechanical Systems, vol. 16, No. 2, 2007, pp. 223-231.

Chen, P.-J. et al. 2008. Floating-Disk Parylene Microvalve for Self-Regulating Biomedical Flow Controls, Technical Digest of the 20th IEEE International Conference on Micro Electro Mechanical Systems (MEMS 2008), Tucson, AZ, USA, Jan. 13-17, 2008, pp. 575-578.

Givrad, T.K. et al. 2008 Implantable Minipump with MEMS Electrothermal Valve for Bolus Injection in Mice. Frontiers in Biomedical Devices, Irvine, California, USA, Jun. 18-20, 2008, BioMed2008.

Li, P.-Y. et al. 2008. Parylene Electrothermal MEMS Drug Delivery Valve. Spring Annual Meeting of the American Chemical Society: Progress in Vapor-Born Poly (p-xylylene)s, Preparation, Properties, Application, New Orleans, Louisiana, USA, Apr. 6-10, 2008, pp. 941-942.

Li, P.-Y. et al. 2008 A Wirelessly-Activated Parylene Electrothermal Valve for Mapping Brain Function in Freely Moving Subjects. Hilton Head 2008: A Solid State Sensors, Actuators and Microsystems Workshop, Hilton Head Island, South Carolina, USA, Jun. 1-5, 2008, pp. 32-35.

Li, P.-Y. et al. 2008. Mechanical and Thermal Modeling of a Parylene Electrothermal Valve for Mapping Brain Function in Freely Moving Subjects. µTAS 2008, Twelfth International Conference on Miniaturized Systems for Chemistry and Life Sciences, San Diego, California, USA, Oct. 12-16, 2008, pp. 1105-1107.

Li, P.-Y. et al. 2008. Parylene Electrothermal Valve for Rapid In Vivo Drug Delivery. American Vacuum Society Topical Workshop on BioMEMS, Boston, Massachusetts, USA, Oct. 19-24, 2008. Abstract only.

Li, P.-Y. et al. 2009. A Parylene MEMS Electrothermal Valve. IEEE/ASME Journal of Microelectromechanical Systems, vol. 18, No. 6, 2009, pp. 1184-1197.

Li, P.-Y. et al. 2010. A Low Power, On Demand Electrothermal Valve for Wireless Drug Delivery Applications. Lab on a Chip, vol. 10, Issue 1, 2010, pp. 101-110.

Lin, J. C.-H. et al. 2009. Minimally Invasive Parylene Dual-Valved Flow Drainage Shunt for Glaucoma Implant, Technical Digest of the 22nd IEEE International Conference on Micro Electro Mechanical Systems (MEMS 2009), Sorrento, Italy, Jan. 25-29, 2009, pp. 196-199.

Lo, R. et al. 2009. In-Plane Bandpass Regulation Check Valve in Heat-Shrink Packaging for Drug Delivery. MEMS 2009, Sorrento, Italy, Jan. 25-29, 2009, pp. 236-239.

Pan, T. et al. 2006. A Reworkable Adhesive-Free Interconnection Technology for Microfluidic Systems. IEEE/ASME Journal of Microelectromechanical Systems, vol. 15, No. 1, 2006, pp. 267-272.

Pan, T. et al. 2006. An Artificial Nano-Drainage Implant (ANDI) for Glaucoma Treatment. 28th Annual International Conference of the IEEE Engineering in Medicine and Biology Society, EMBS '06., New York, NY, Aug. 30-Sep. 3, 2006, pp. 3174-3177.

Wang, X.-Q. et al. 2000. A Normally Closed In-Channel Micro Check Valve, Technical Digest of the 14th IEEE International Conference on Micro Electro Mechanical Systems (MEMS 2000), Miyazaki, Japan, Jan. 23-27, 2000, pp. 68-73.

Xie, J. et al. 2001. Surface Micromachined Leakage Proof Parylene Check Valve, Technical Digest of the 14th IEEE International Conference on Micro Electro Mechanical Systems (MEMS 2001), Interlaken, Switzerland, Jan. 21-25, 2001, pp. 539-542.

International Search Report and Written Opinion of the International Searching Authority (Korean Intellectual Property Office), mailed Oct. 19, 2010, for PCT Application No. PCT/US2010/024730, filed Feb. 19, 2010 (international application corresponding to U.S. Appl. No. 12/709,188).

International Search Report and Written Opinion of the International Searching Authority (Korean Intellectual Property Office), mailed Jan. 18, 2011, for PCT Application No. PCT/US2010/024808, filed Feb. 19, 2010 (international application corresponding to U.S. Appl. No. 12/709,335).

\* cited by examiner

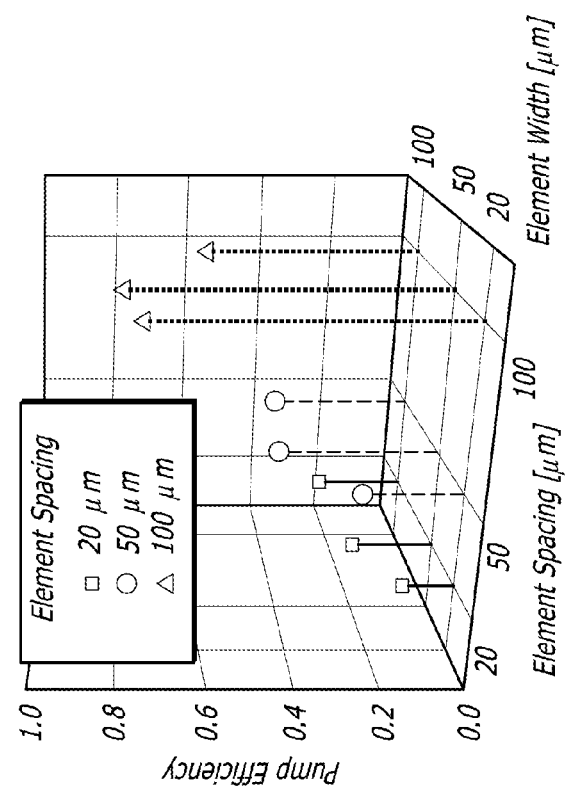
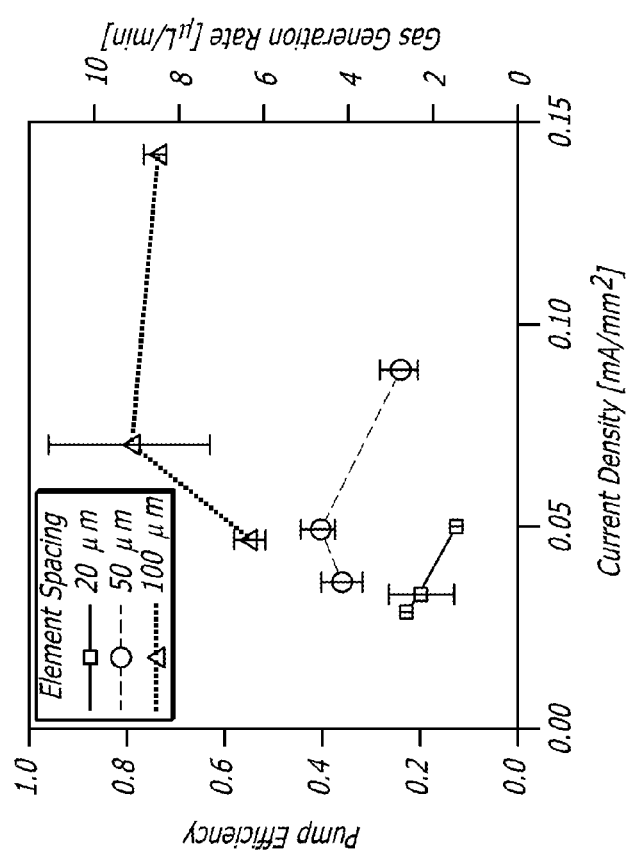
FIG. 9b
FIG. 9a

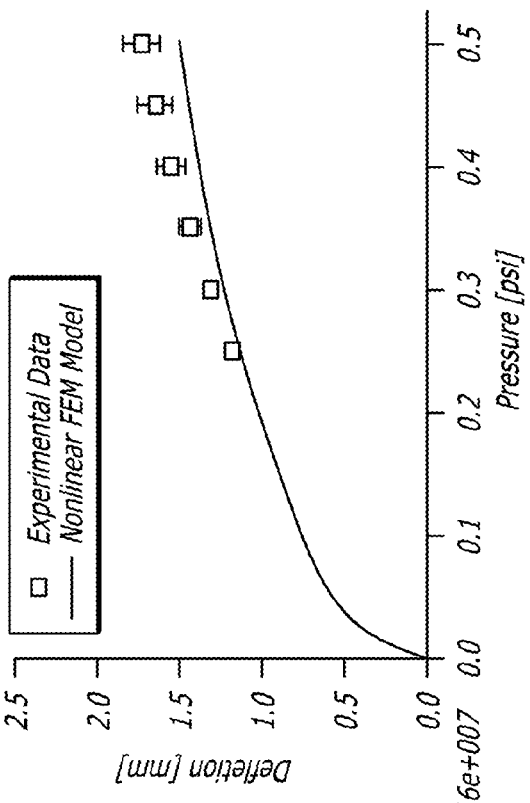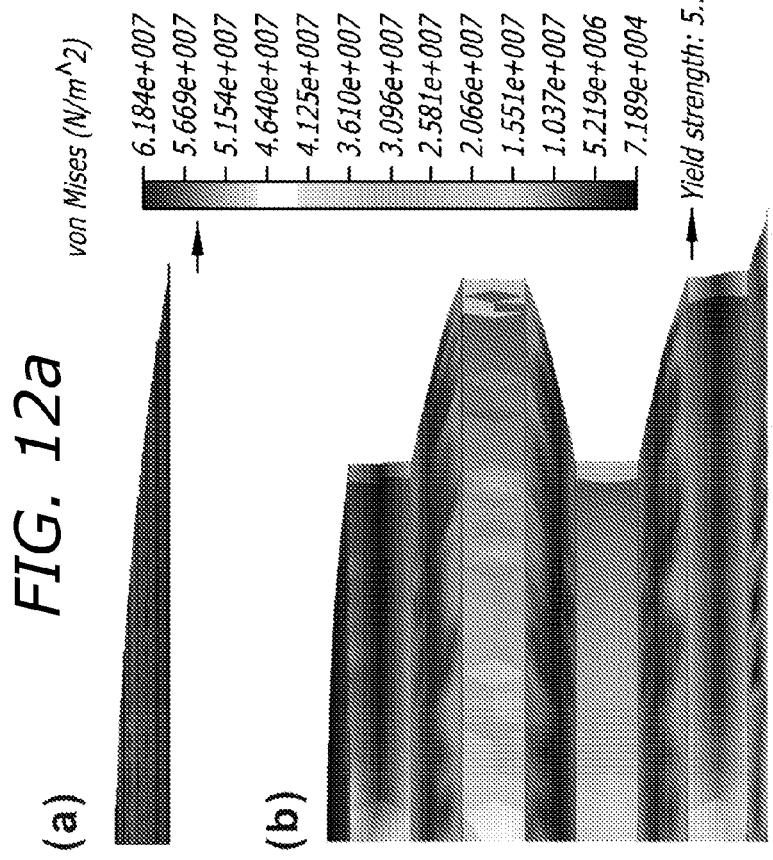
FIG. 12a  FIG. 12b  FIG. 12c

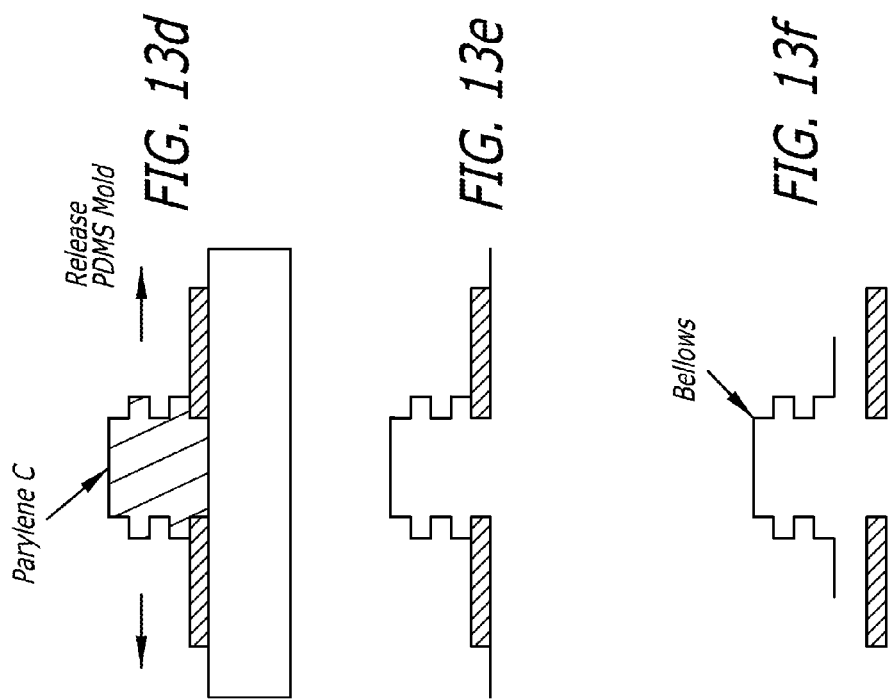
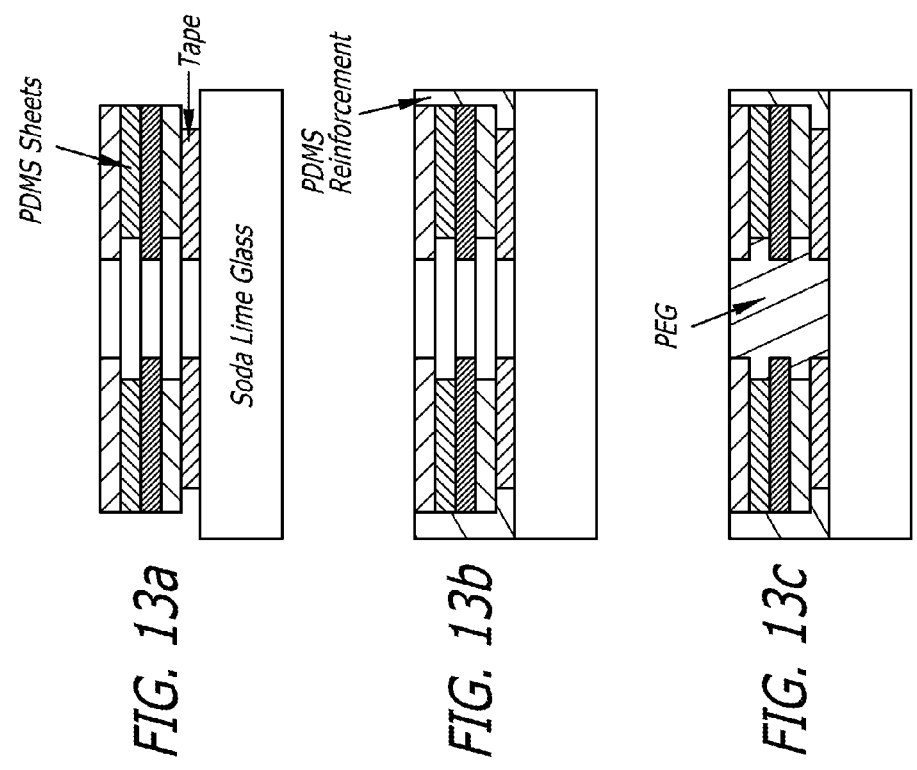

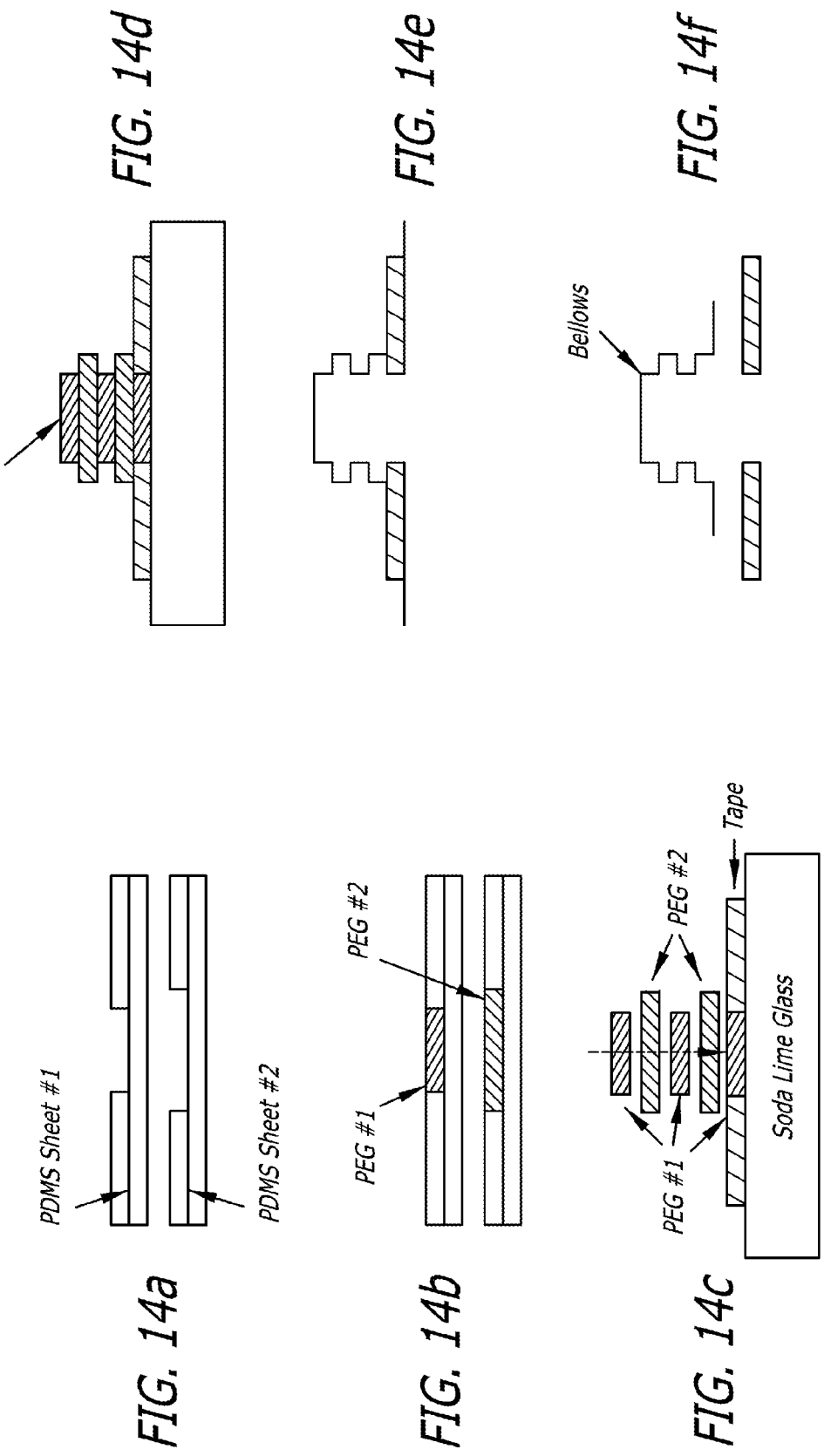

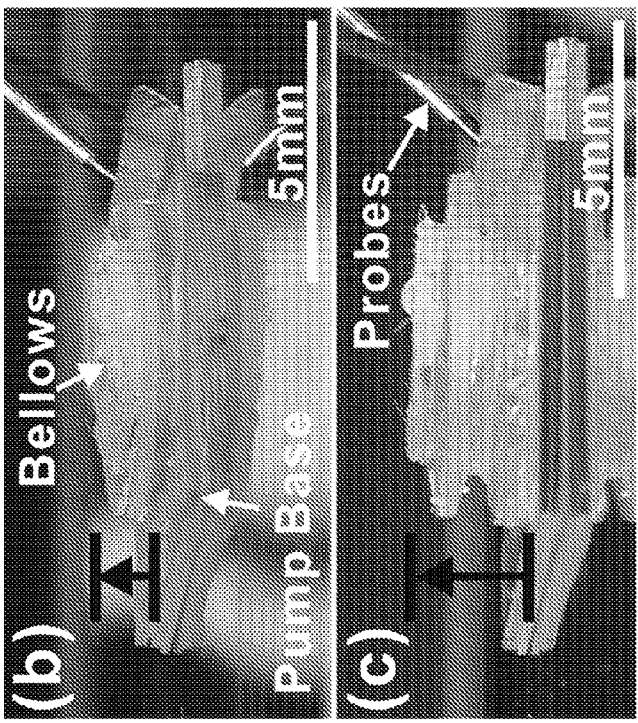
FIG. 18b
FIG. 18c
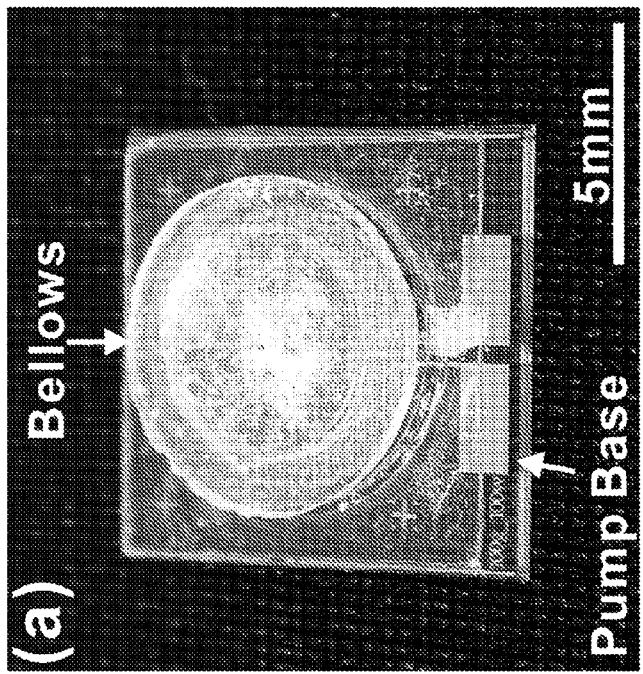
FIG. 18a

Steady-State Mode

Electrolysis Mode

Recovey Mode

From main drug reservoir

MEMS ELECTROCHEMICAL BELLOWS ACTUATOR

CROSS-REFERENCE TO RELATED APPLICATIONS

This application is based upon and claims priority to U.S. Provisional Patent Application No. 61/154,327, entitled "MEMS ELECTROCHEMICAL BELLOWS ACTUATOR," filed Feb. 20, 2009; U.S. Provisional Patent Application No. 61/266,978, entitled "ELECTROCHEMICAL BELLOWS FLUID DOSING DEVICE," filed Dec. 4, 2009; and U.S. Provisional Patent Application No. 61/266,977, entitled "RADIATION-DOSE REDUCTION USING siRNA NANOPARTICLE DELIVERY VIA MEMS-BASED PUMPS," filed Dec. 4, 2009.

This application is also related to U.S. Provisional Patent Application No. 60/154,314, entitled "IN-PLANE BANDPASS REGULATION CHECK VALVE IN HEAT-SHRINK PACKAGING FOR DRUG DELIVERY," filed Feb. 20, 2009; and U.S. patent application Ser. No. 12/709,188 (now U.S. Pat. No. 8,372,046 B2, issued Feb. 12, 2013), entitled "DRUG DELIVERY DEVICE WITH IN-PLANE BANDPASS REGULATION CHECK VALVE IN HEAT-SHRINK PACKAGING," which was filed on the same day as this application.

STATEMENT REGARDING FEDERALLY SPONSORED RESEARCH

This invention was made with Government support under Grant No. R21EY018490 awarded by the National Institutes of Health. The Government has certain rights in the invention.

BACKGROUND

1. Technical Field

This disclosure relates to microelectromechanical systems (MEMS), including implantable microfluidic drug delivery systems.

2. Description of Related Art

Microfluidic drug delivery systems can be implanted in living organisms, such as in the eye of a human being. These systems may include a storage reservoir which stores a fluidic drug, an actuator which controllably expels the fluid drug from the storage reservoir, and a cannula which transfers the expelled fluid from the storage reservoir to a delivery location.

Different types of actuators have been used, including interdigitated electrochemical microelectrode pumps, microbellows, and electrolysis diaphragm actuators. These actuators may be made separately and integrated into the system. These actuators may include a diaphragm and a pump base having a pair of electrodes. When current is applied, electrolysis may take place, breaking an electrolyte into oxygen and hydrogen gases. These gases may force the diaphragm to expand. The expansion of the diaphragm, in turn, may expel fluid from the storage reservoir.

There can be difficulties with these implantable devices. During electrolysis, for example, the diaphragm may yield less-than-desirable performance (e.g., large dead volume, large stress/strain anchor points, durability, and limited expansion). The pumps may also have limited range of use or applications because they may not be scalable in size (e.g., for use in a mouse). Another concern may be with interdigitated electrodes used for the electrolysis. The associated electrolysis power efficiency (less than 50%), performance, and durability of the microelectrode may be unreliable and highly dependent on the design and fabrication process of the electrode. When the device is off and no electrolysis is taking place, there may be an uncontrolled release of fluid from the dispensing orifice. The gases may also recombine to reverse the pressure gradient and may create a suction, pulling in the fluid that had just been dispensed into the body at the orifice of the cannula. Over the life cycle of the device, the fluid reservoir may decrease in volume as fluid is dispensed. This dynamic and ever-decreasing volume of dispense fluid may make it difficult to calculate the actual fluid dispensing rate at any given time. It may also be difficult to refill and/or change the contents of the reservoir, as well as to extract a fluid sample from the living host.

SUMMARY

An implantable fluid delivery system may include a fluid reservoir configured to hold a supply of fluid, to dispense that fluid under the control of an actuator, and to be implanted within the body of a living host. An actuator within the fluid reservoir may cause the fluid to be controllably dispensed from the fluid reservoir. The actuator may include a bellows configured to expand when inflated. The bellows may have folds with surfaces which run substantially perpendicular to the direction of expansion in a collapsed state and which define a stacked set of convolutions. Each convolution may have a collapsed height of no more than 1 mm and a width perpendicular to the direction of expansion of no more than 8 mm. Electrodes may be configured to come in electrical contact with an electrolyte within the bellows and to cause electricity to run through the electrolyte, thereby causing the electrolyte to break down into a gas and, in turn, to cause the bellows to expand.

The implantable fluid delivery system may be configured to fit within a human eye.

The implantable fluid delivery system may be configured such that the fluid and the electrolyte cannot mix. The actuator may create a sealed chamber from which the electrolyte cannot leak.

The stacked set of convolutions may taper in width.

The bellows may be made of Parylene C.

A method for making bellows which expands in a direction when inflated may include stacking stencil sheets. Each stencil sheet may have a within the stencil sheet which corresponds to the shape of the exterior surface of a cross-sectional slice of the bellows. The stacked stencil sheets may collectively form a cavity, the interior of which may collectively correspond to the shape of the exterior surface of the bellows. The cavity formed by the stacked stencil sheets may be filled with a filler. The filler may be removed from within the stacked stencil sheets after it has hardened. The hardened filler may be coated with a coating. The coating may be removed from the hardened filler after the coating has hardened. The removed and hardened coating may be used as the bellows.

The method may include placing tape on a substrate prior to stacking the stencil sheets of material. The stencil sheets may be stacked on the tape.

The stencil sheets may be made of PDMS.

The filler may be made of PEG.

The coating may be made of Parylene C.

An alternate method for making a bellows which expands in a direction when inflated may include stacking filler subunits made from individual stencil sheets. Each stencil sheet may have an opening that may be filled with filler. The shape of the opening may define the perimeter surface of the filler subunit which corresponds to the shape of the exterior surface of a cross-sectional slice of the bellows. The filler subunits may be stacked and collectively form a hardened filler structure, the exterior of which may collectively correspond to the shape of the exterior surface of the bellows. The hardened filler may be coated with a coating. The hardened filler may be removed. The coating with the hardened filler removed may be used as the bellows.

The method may include forming a stencil sheet with an opening which corresponds to each unique shape of the perimeter surface of each mold sheet before the stacking. The cavities formed by the openings may be filled with a filler before the stacking. The filler may be removed from each mold sheet after it has hardened and before the stacking. The removed and hardened fillers may be used as the mold sheets.

The method may include placing tape on a substrate prior to stacking the mold sheets. The mold sheets may be stacked on the tape.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details which may be apparent or unnecessary may be omitted to save space or for more effective illustration. Conversely, some embodiments may be practiced without all of the details which are disclosed. When the same numeral appears in different drawings, it refers to the same or like components or steps.

FIGS. 9A and 9B illustrate pump geometry optimization results based on the current-controlled flow delivery for the drug delivery electrolysis system.

FIGS. 12A-12C illustrate modeling and experimental testing results of Parylene membranes.

FIGS. 13A-13F illustrate a molding process which may be used to mold thin film polymer bellows by stacking poly dimethylsiloxane (PDMS) sheets.

FIGS. 14A-14F illustrate a molding process which may be used to mold thin film polymer bellows by stacking PEG molds.

FIG. 17A illustrates an exploded view of the components.

FIGS. 18A-18C are photographs of pump actuation.

DETAILED DESCRIPTION OF ILLUSTRATIVE EMBODIMENTS

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

An electrochemical actuator may use Parylene bellows for intraocular delivery of medication at therapeutic levels. The actuator may separate the electrochemical actuation from the drug reservoir using the Parylene bellows.

The Parylene may be fabricated using a polyethylene glycol (PEG)-molding process. The gas generation efficiency of electrolysis-based actuators may be optimized. Efficiency approaching 80% and over 1.5 mm deflection with this optimized actuator may be achieved.

The actuator which may be optimized for ocular drug delivery. The electrochemical reaction of the actuator may be separated from the drug to prevent unwanted pH changes or drug degradation. A robust, high deflection Parylene bellows may be used. The electrochemical actuator electrodes may be optimized for efficiency.

Figure 1:
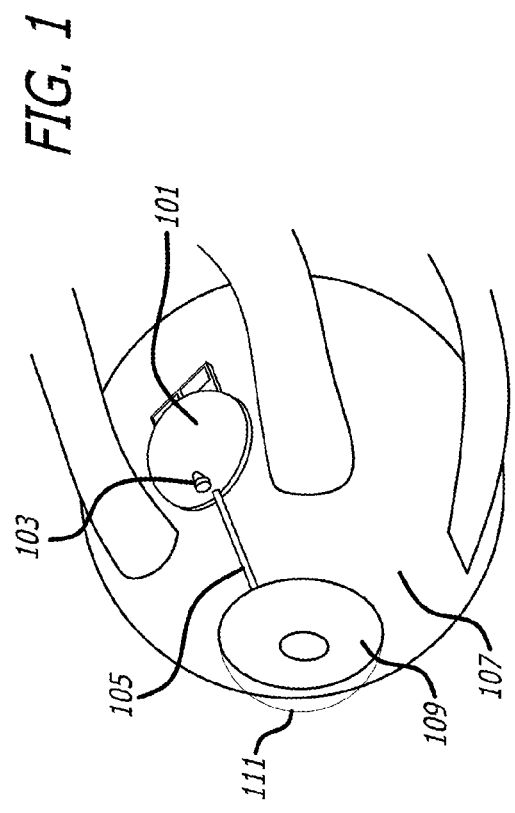
FIG. 1 illustrates a drug delivery system with an optimized actuator.

FIG. 1 illustrates a drug delivery system with an optimized actuator. The system may include a drug reservoir 101 configured to store a fluidic drug, a refill port 103 configured to allow the reservoir to be refilled and/or for the drug to be removed and/or tested, and a cannula 105 through which the drug may flow from the drug reservoir 101.

The system may be implanted into an eye 107 having an iris 109 and a cornea 111. The drug may be delivered through the cannula 105 within the eye and directed at a site of therapy. The drug delivery system may instead be implanted in other parts of a living body.

Figure 2:
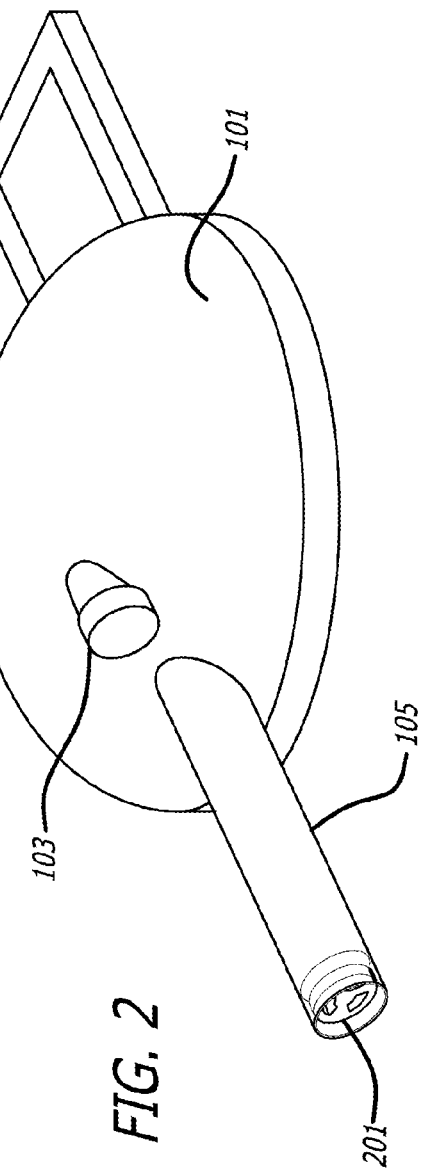
FIG. 2 illustrates an enlarged view of the drug delivery system illustrated in FIG. 1.

FIG. 2 illustrates an enlarged view of the drug delivery system illustrated in FIG. 1. A pressure regulating valve 201 may be inserted into the cannula 105 to regulate the flow of the drug. Examples of such valves and their possible locations are described in U.S. patent application entitled "DRUG DELIVERY DEVICE WITH IN-PLANE BANDPASS REGULATION CHECK VALVE IN HEAT-SHRINK PACKAGING," which is being filed on the same day as this application, the entire contents of which are incorporated herein by reference.

Figure 3:
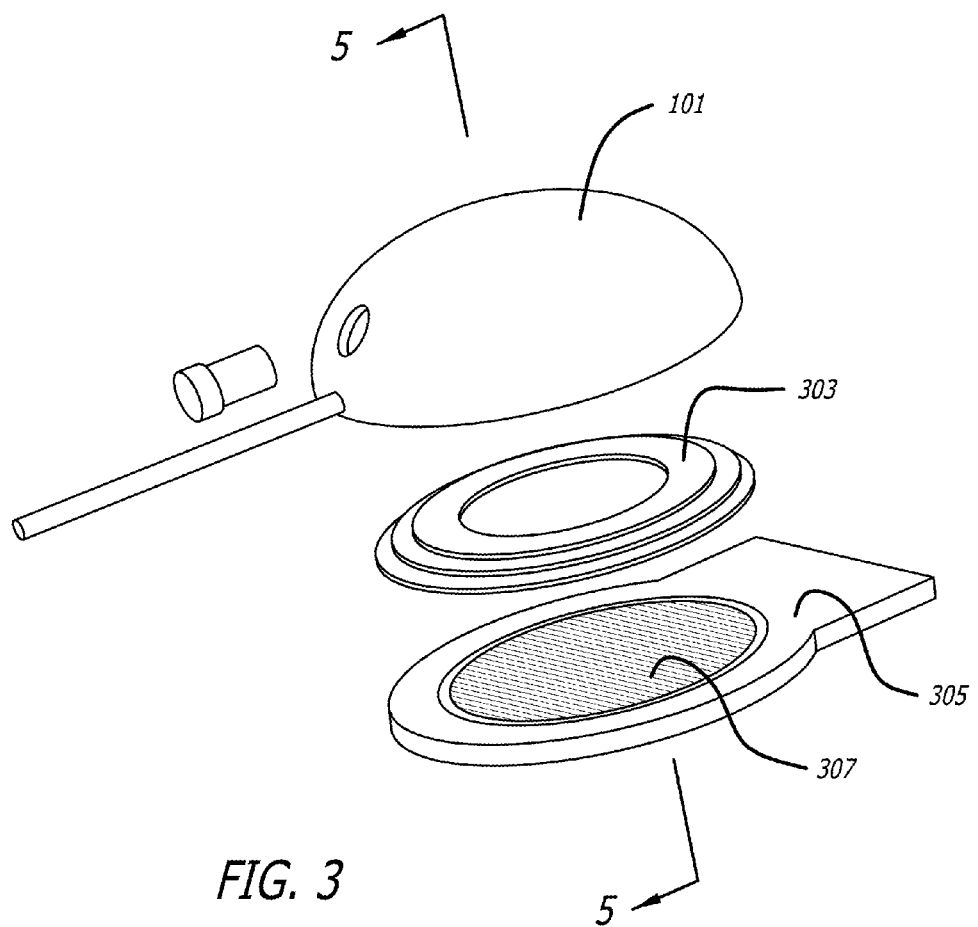
FIG. 3 is an exploded view of various components in the drug delivery system illustrated in FIG. 2.

FIG. 3 is an exploded view of various components in the drug delivery system illustrated in FIG. 2. The system may include the drug reservoir 101 and a pump within the drug reservoir 101. The pump may include a bellows 303 which may be made of a Parylene membrane or other material, a pump base 305, and electrodes 307.

Figure 4:
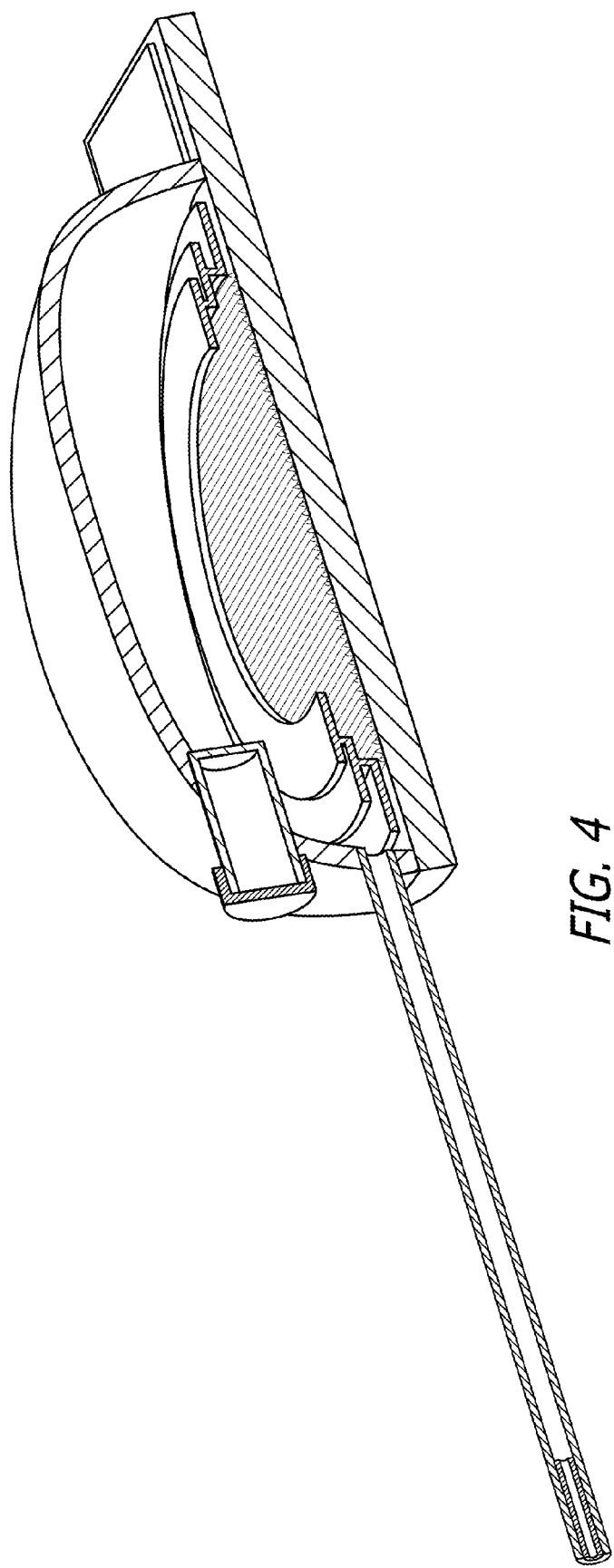
FIG. 4 is a cut-away view of FIG. 3.

FIG. 4 is a cut-away view of FIG. 3.

Figure 5A:
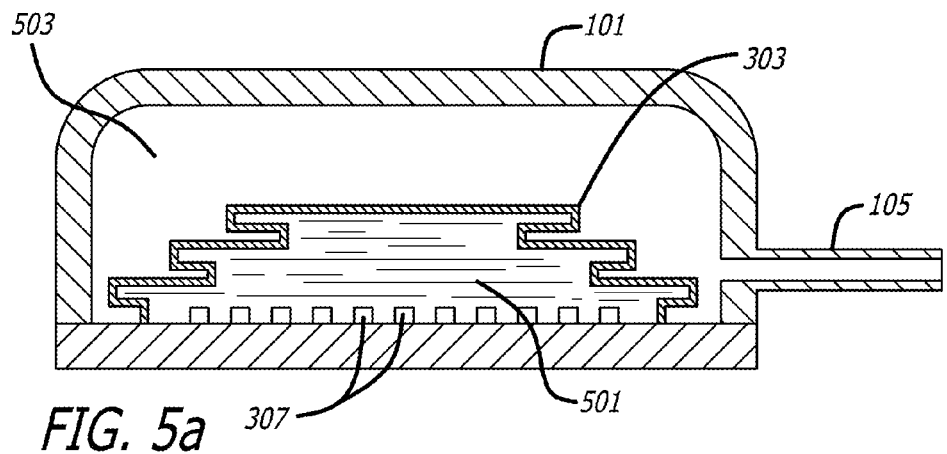
FIGS. 5A and 5B is a cross-sectional view of the drug delivery system illustrated in FIG. 3 taken along the line 5-5' during different stages of operation.
Figure 5B:
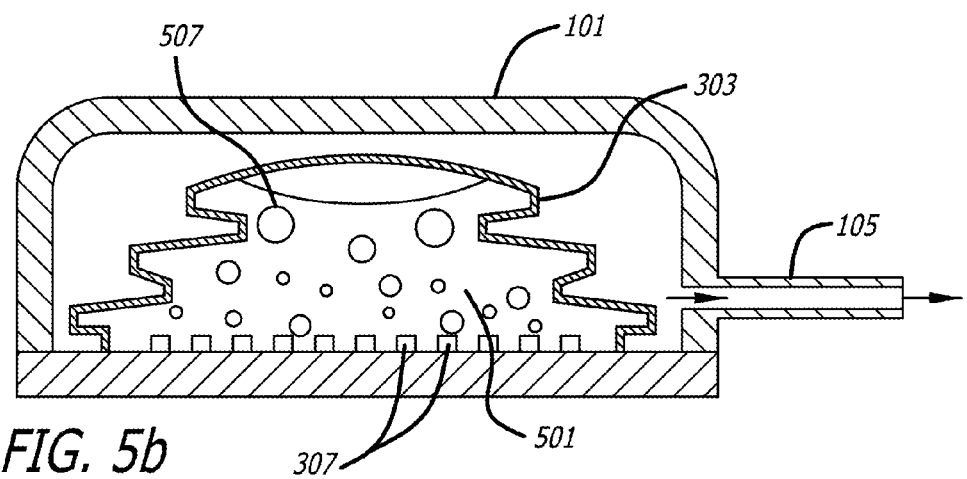

FIGS. 5A and 5B is a cross-sectional view of the drug delivery system illustrated in FIG. 3 taken along the line 5-5' during different stages of operation. Electricity may be applied to the electrodes 307 which may be made of platinum, titanium, and/or other material. This may cause electrolysis of fluid 501, such as deionized water, which has been placed between the bellows 303 and the pump base 305. In turn, this may generate hydrogen and oxygen gas 507. The fluid may be water or any other fluid which is subject to an electrolytic reaction when electricity is passed through it.

In turn, this may cause the bellows 303 to expand. In turn, this may cause fluidic drug 503 to be pumped into the cannula 105 which may be expelled at the other end of the cannula at a target location, such as a target location in the eye. The bellows 303 may be sealed to the pump base 305 so that the fluidic drug 503 within the drug reservoir 101 cannot mix with the fluid 501 or the gas 507 that may be sealed within the bellows 303.

The basic geometry in FIGS. 5A and 5B shows one actuated drug chamber. For applications in which multiple drugs or mixtures of drugs are dosed, the drug reservoir 101 may be configured to have multiple chambers, each with a separate actuator and associated cannula or a multi-lumen cannula. This may enable delivery of multiple drugs at the same or distinct locations nearby the drug reservoir 101. For delivery of drug mixtures, multiple actuated reservoirs may feed a mixer that may feed a single cannula or multiple cannulae for delivery to a specific location or multiple locations, respectively.

Figure 6:
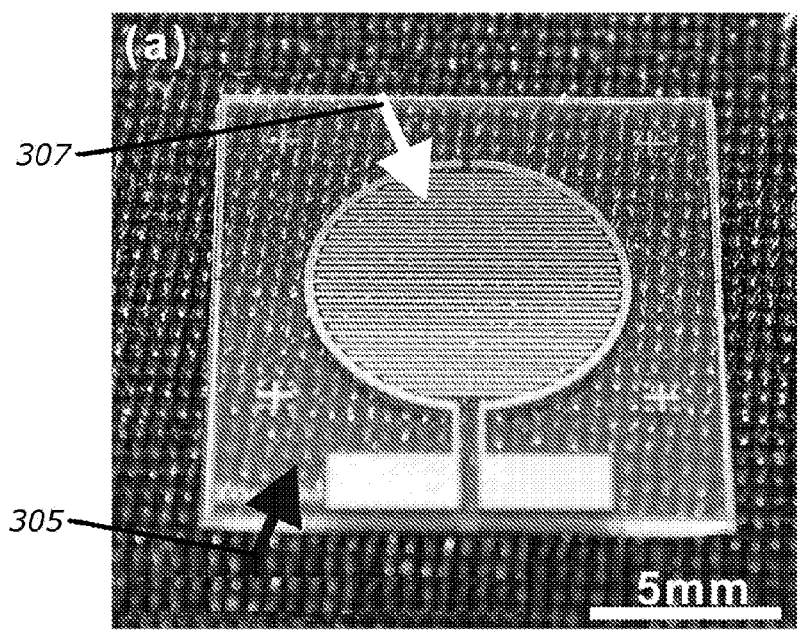
FIG. 6 is a photograph of a pump base which may include a soda lime glass substrate and fabricated interdigitated Pt/Ti electrolysis electrodes.

FIG. 6 is a photograph of a pump base 305 which may be include a soda lime glass substrate and fabricated interdigitated Pt/Ti electrolysis electrodes 307. The pump base may be fabricated separately from the bellows 303 and then joined together in a fashion that seals fluid within the structure.

Figure 7A:
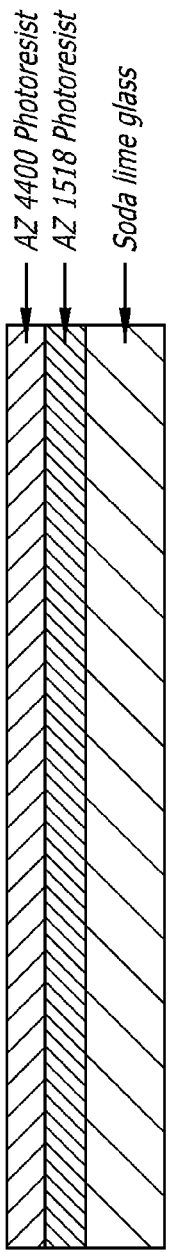
FIGS. 7A-7D illustrate a fabrication process that may be used to fabricate the pump base and the electrodes.
Figure 7B:
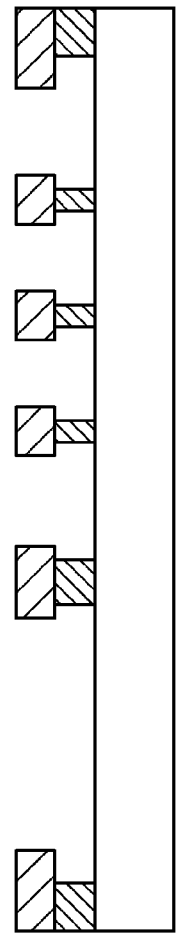
Figure 7C:
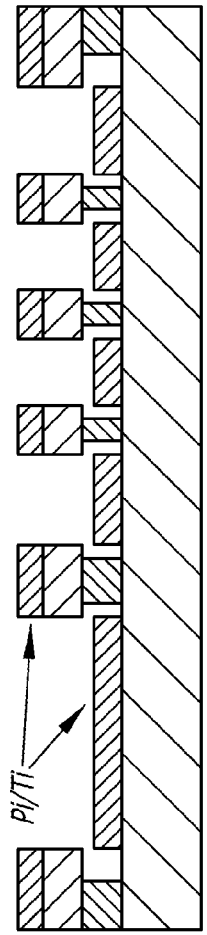
Figure 7D:
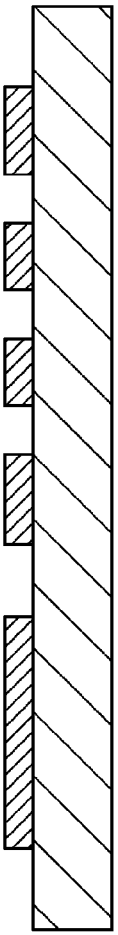

FIGS. 7A-7D illustrate a fabrication process that may be used to fabricate the pump base 305 and the electrodes 307. FIG. 7A illustrates a spun-on dual-layer photoresist (AZ1518 and AZ4400) which may be used to create undercut for Pt liftoff. FIG. 7B illustrates the result of UV exposure which may define the pattern of the dual-layer photoresist. FIG. 7C illustrates an e-beam evaporation of Pt/Ti (2000 Å/300 Å). FIG. 7D illustrates Pt liftoff which may define the interdigitated microelectrodes and contact pad patterns.

The electrodes may be fabricated using standard thin film processes. Thin film processes that may be used to deposit metallic electrodes include but are not limited to thermal evaporation, electron beam evaporation, and sputtering. Non-planar, 3D electrodes may be produced by methods such as electroplating, electroless plating, metal forming, and other techniques. In this case, three-dimensional may be distinguished from thin film in that the geometry of the electrodes may not be planar, have a rectangular cross section, or have a thickness much less than the lateral dimension (length and width). Metals and alloys, such as Pt, Pt/Ti, or others may be used to increase or decrease efficiency of the electrolysis reaction. Optimization experiments described below use deionized water as the electrolyte. Other electrolyte mediums may be substituted.

To determine design parameters for optimal pump efficiency and to decrease power consumption, a series of interdigitated electrolysis electrodes may be fabricated having different element widths and spacings. Table 1 below lists examples of these widths and spacings.

TABLE 1

Electrode parameters for drug delivery electrolysis pump optimization

| Element Width (µm) | Element Spacing (µm) | Electrode Area (mm²) |
|---|---|---|
| 20 | 20 | 20.0 |
| 20 | 50 | 29.8 |
| 20 | 100 | 34.6 |
| 50 | 20 | 11.2 |
| 50 | 50 | 20.2 |
| 50 | 100 | 27.4 |
| 100 | 20 | 7.0 |
| 100 | 50 | 14.2 |
| 100 | 100 | 21.4 |

Figure 8:
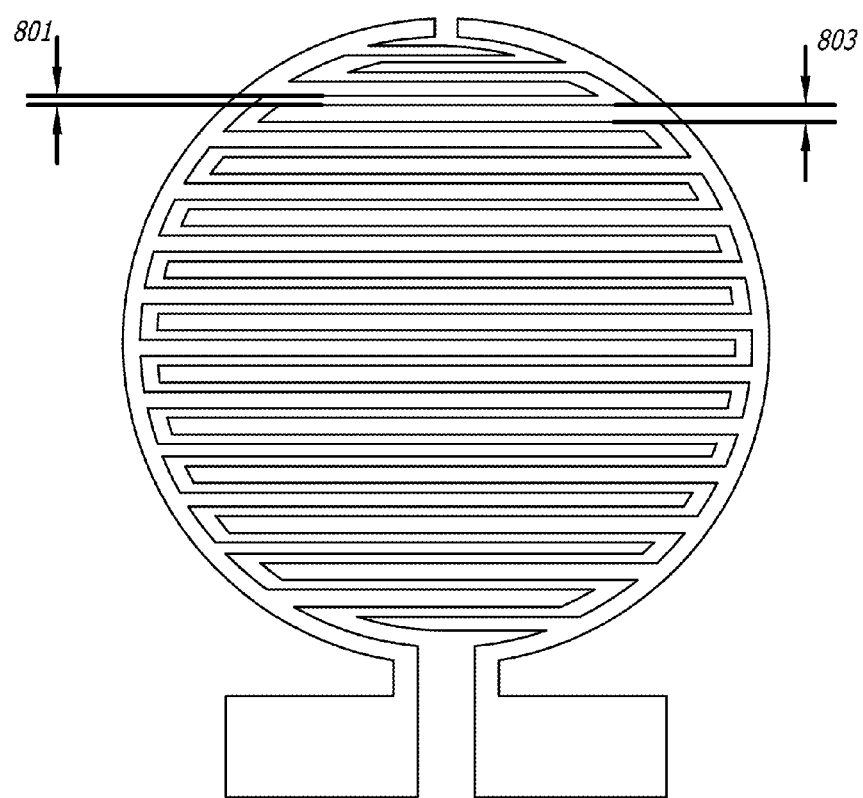
FIG. 8 illustrates the location of the element spacings and the element widths 803 that are set forth in Table 1.

FIG. 8 illustrates the location of the element spacings 801 and the element widths 803 that are set forth in Table 1.

FIGS. 9A and 9B illustrate pump geometry optimization results based on the current-controlled flow delivery for the drug delivery electrolysis system. FIG. 9A illustrates the relationship of pump efficiency and gas generation rate to current density. FIG. 9B illustrates the relationship of pump efficiency to element spacing and element width. The gas generation rate and corresponding pumping efficiency under a constant 1 mA applied current may be measured and calculated. The gas generation rate was measured as the water flow rate resulting from electrolysis actuation using a calibrated pipette. Efficiency improved with increasing element spacing while a peak efficiency exists in relation to current density and element width. The best performance may be achieved with 50 µm elements having 100 µm spacing (efficiency of ~80% compared to 49%).

Further improvement in electrolysis efficiency may be gained beyond the manipulation of interdigitated electrode element width and spacing. Three-dimensional electrodes with greater surface area and roughness may be formed by electroplating additional metal on top of the evaporated thin film electrodes.

One method of electroplating is described below to modify the As-deposited electrodes. However, electrodes of greater thickness, surface area, and surface roughness may be achieved through a number of metal pattern form methods including, but not limited to, die cutting, wire forming, electroplating, and welding.

Circular interdigitated electrodes with an element width of 100 µm and element spacing of 20 µm were electroplated to increase the electrode surface roughness to demonstrate its impact on pump efficiency. The gas generation rate before electroplating was first measured. The electrodes were then connected to a potentiostat (e.g., Potentiostat 273A, Princeton Applied Research, Oak Ridge, Tenn.) in a three-electrode cell configuration with an Ag/AgCl reference electrode. The electroplating solution consisting of $(NH_4)_2PtCl_6$ was held at a near neutral pH of ~7.8 See Whalen, J., J. Weiland, and P. Searson, *Electrochemical Deposition of Platinum from Aqueous Ammonium Hexachlooplatinate Solution*. Journal of the Electrochemical Society, 2005. 152: p. C738-43. Potentiostatic deposition (−0.5 V for 15 min) was performed and then the devices were flushed with DI water and blown dry with filtered $N_2$. Cyclic voltammetry (CV) and electrochemical impedance spectroscopy (EIS) were used to characterize the surface roughness of the electrodes before and after electroplating. $H_2SO_4$ (0.5 M) was used as the electrolyte in both cases. Finally, the gas generation rate of the electroplated device was measured (applied current of 0.2-0.8 mA) to obtain a before-after comparison.

The bellows illustrated in FIGS. 5A and 5B may have a broad variety of shapes and configurations. In general, the bellows may include a hollow tube having an enclosing wall, such as a cylindrical or rectangular wall. The bellows may include segments that have alternating increasing or decreasing radial distances from the central axis of the tube. The wall may bend either in or out in an alternating pattern of convex and concave angles.

A convolution within a bellows is the smallest flexible unit of the repeated pattern in the bellows.

Figure 10A:
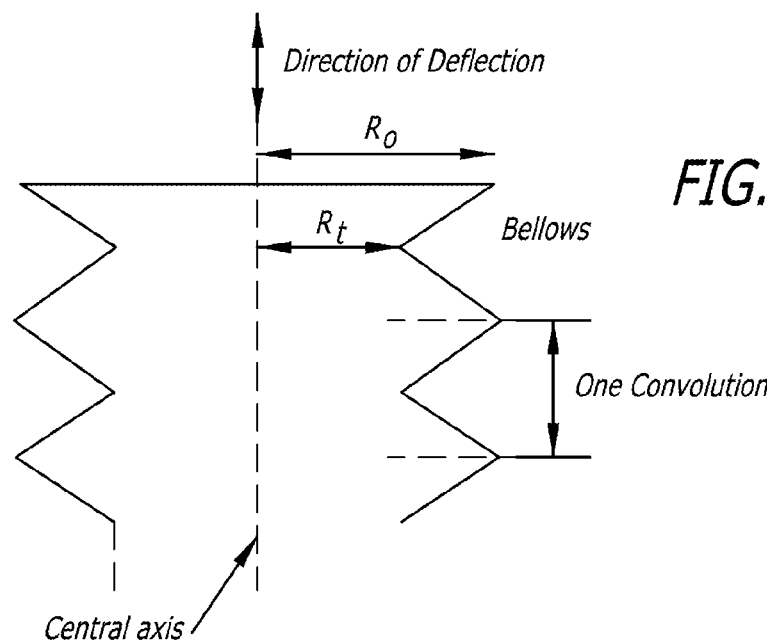
FIGS. 10A and 10B illustrate the concept of a convolution within two different configurations of bellows.
Figure 10B:
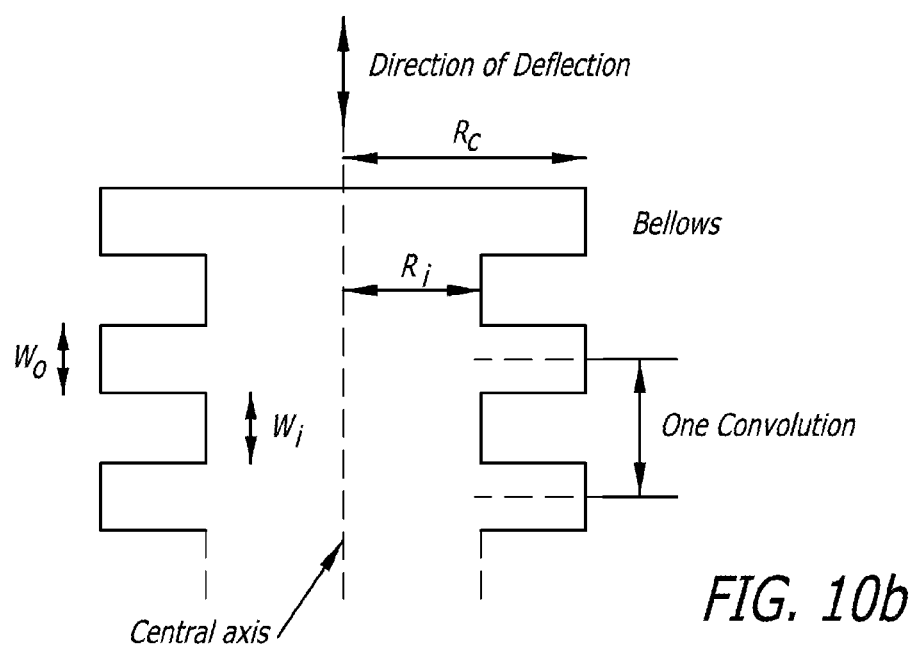

FIGS. 10A and 10B illustrate the concept of a convolution within two different configurations of bellows. FIG. 10A illustrates a bellows with convolutions having a triangular cross-section while in a collapsed state; and FIG. 10B illustrates a bellows with convolutions that have a rectangular cross-section while in a collapsed state. A convolution includes the portion of the wall that includes the largest radial distance (Ro) and the portion of the wall that includes the shortest radial distance (Ri).

The radial distances may be in any amount. For example the largest radial distance among all of the bellows may be no more than 4 mm or 8 mm in diameter.

The collapsed and expanded height of each convolution and the collective effect on the bellows may be in any amount. For example, the collapsed height of each convolution may be no more than 1 mm.

The convolutions of a bellows may not have vertices. Instead, the convolutions may have the shape of another polygon or possess a rounded shape. For example, at the two extreme distances (Ro and Ri), the segments may join to form a square or rectangular convolution when collapsed having segment widths of Wo and Wi when viewed from a cross-section of the bellows, as illustrated in FIG. 10B.

The cross-section of the bellows in a plane that is perpendicular to the direction of motion may have any configuration, such as circular, oval, triangular, or rectangular.

Figure 11A:
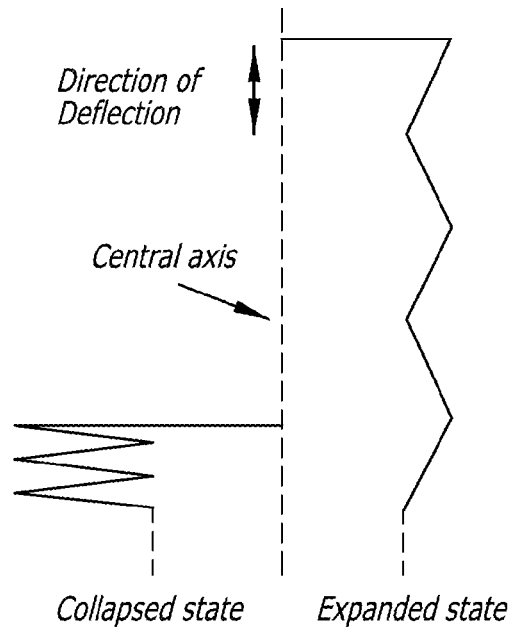
FIGS. 11A and 11B illustrate different configurations of bellows in both a collapsed and an expanded state.
Figure 11B:
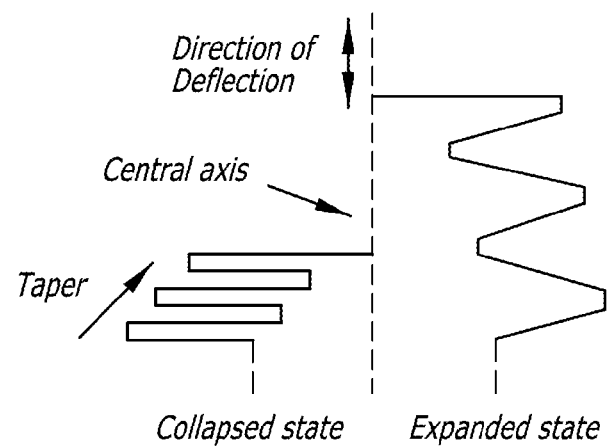

FIGS. 11A and 11B illustrate different configurations of bellows in both a collapsed and an expanded state. FIG. 11A illustrates a bellows having convolutions with a triangular cross-section in a collapsed state; while FIG. 11B illustrate a bellows having convolutions with a rectangular cross section in a collapsed state. As also illustrated in FIG. 11B, the width of the convolutions may decrease in the direction of travel, creating a tapered cross-section. This is also the configuration illustrated in FIGS. 5A and 5B.

The bellows may be configured to provide a large deflection with lower material stress. A nonlinear FEM analysis was performed using a quarter models.

FIGS. 12A-12C illustrate modeling and experimental testing results of Parylene membranes. FIG. 12A illustrates finite element modeling results for a corrugated membrane. FIG. 12B illustrates finite element modeling results for a bellows. FIG. 12A illustrates the experimental deflection vs. pressure results and those simulated by the linear bellow approximation and a nonlinear finite element model.

The simulation confirms the larger bellows deflection of 1.5 mm versus 0.8 mm under 0.5 psi (3.44 kPa) applied pressure and 10 μm membrane thickness. The maximum stress of the bellows was 61.8 MPa (less than Parylene tensile strength, 68.9 MPa).

Load deflection experiments were performed and showed good agreement with the nonlinear simulations. Experimentally, an average maximum deflection of 1.783 mm was obtained under 0.5 psi applied pressure, as reflected in FIG. 12C.

FIGS. 13A-13F illustrate a molding process which may be used to mold thin film polymer bellows by stacking poly dimethylsiloxane (PDMS) sheets. FIG. 13A illustrates stack spin casted PDMS sheets with pre-cut holes on a masked glass (tape) to form a master mold. FIG. 13B illustrates reinforcing the mold edge with more PDMS, and curing at 65° C. for 1 hour. FIG. 13C illustrates filling liquid polyethylene glycol (PEG) (at 80° C.) into the master and evacuating to eliminate gas bubbles. FIG. 13D illustrates, after cooling, releasing the PEG mold from PDMS master and then coating the bellows mold with Parylene C (10 μm). FIG. 13E illustrates releasing the tape with Parylene coated PEG and immersing the whole structure into DI water (80° C.) to dissolve the PEG. FIG. 13F illustrates releasing the Parylene bellows from the tape.

FIGS. 14A-14F illustrate a molding process which may be used to mold thin film polymer bellows by stacking PEG molds. FIG. 14A illustrates stack spin casted PDMS sheets with pre-cut holes to form PDMS molds; FIG. 14B illustrates filling liquid PEG (at 80° C.) into the PDMS molds and evacuating to eliminate gas bubbles; FIG. 14C illustrates, after cooling, releasing the PEG molds from the PDMS molds and then stacking the PEG molds on a masked glass (tape); FIG. 14D illustrates coating the bellows mold with Parylene C (10 μm); and FIG. 14E illustrates releasing the tape with Parylene coated PEG and immersing the whole structure into DI water (80° C.) to dissolve PEG; and FIG. 14F illustrates releasing the Parylene bellows from the tape.

Figure 15C:
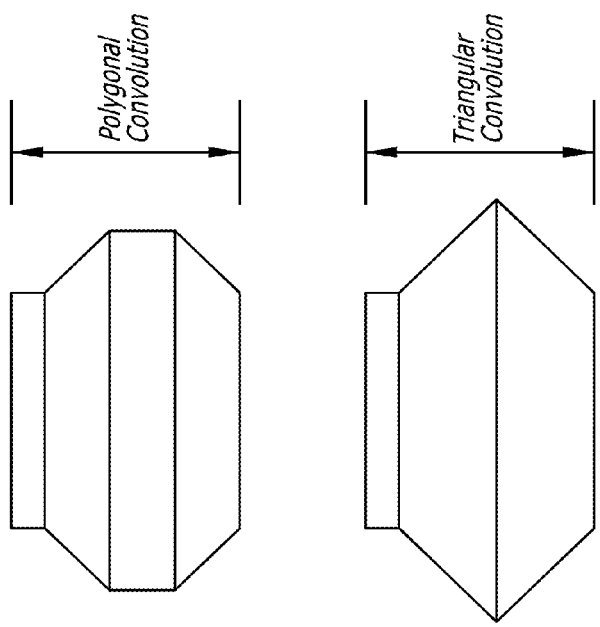
FIGS. 15A-15C illustrate a cross-section of stacked PEG molds forming a single convolution.
Figure 15B:
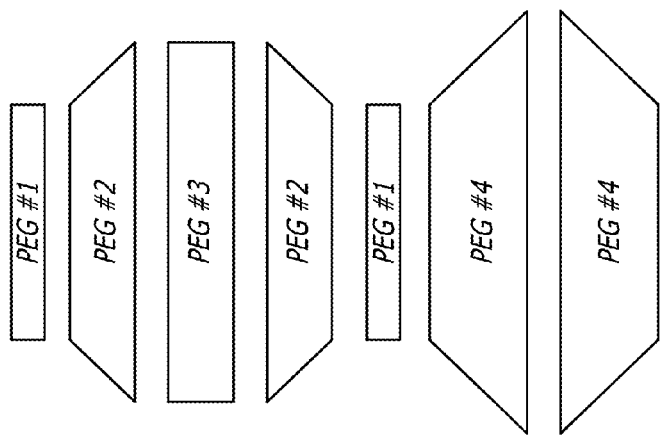
Figure 15A:
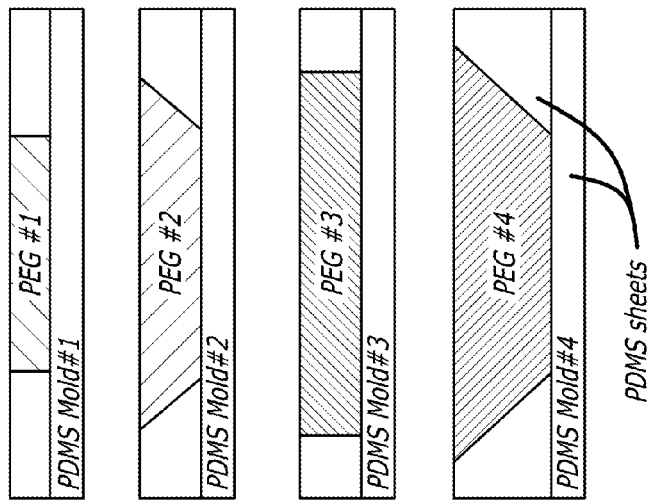

FIGS. 15A-15C illustrate a cross-section of stacked PEG molds forming a single convolution. FIG. 15A illustrates stacked PDMS sheets which may form individual PDMS molds. As illustrated in FIG. 15A, an individual sheet may have a slanted exterior perimeter surface which may be helpful when making convolutions that have a triangular cross-section. FIG. 15B illustrates PEG molds which may be made from the PDMS sheets. As illustrated in FIG. 15B, a single PDMS sheet may be used to produce multiple PEG molds of the same shape. FIG. 15C illustrates assembled stacks of the PEG molds, one forming a structure for a convolution having a polygon cross-section, another forming a structure for a convolution having a triangular cross section. Replicas of each structure may be stacked upon one another to create the composite mold for an entire bellows.

As illustrated in FIGS. 13A-13F and 14A-14F, the bellows fabrication process may involve the layer-by-layer definition of each convolution. In this manner, a variety of bellows convolution geometries and the overall shape of the bellows profile may be specified. First, soft polymer sheets (such as polydimethylsiloxane (PDMS), or silicone rubber) may be casted and die cut, such as with a circular die. Other materials for this step may be employed, such as metals for this step. In the examples shown in FIGS. 13A and 13B, each sheet may define a portion of the bellows; one sheet may contain a circular through hole having a smaller diameter; and the other sheet may contain a circular through hole having a slightly larger diameter. Together, the smaller and larger diameters may correspond to the inside and outside diameter of the bellows, respectively. The thickness of each sheet may also determine the overall thickness of each convolution. The inside and outside diameter of each bellows need not be the same. Some applications may require a bellows having a tapered profile (successively smaller inner and outside diameters as measured from the base of the bellows).

The dies used to cut the sheets may have perpendicular or angled side walls when viewed in cross-section. The individual polymer sheets may also be casted around forms which may be cylindrical with pre-defined shapes corresponding to a portion of or a whole convolution FIGS. 13B and 13C. The sheets may then be separated and stacked to form the desired bellows shape.

The sheets may be stacked together in alternating order of smaller and larger diameters to form the overall bellows shape. In the example shown in FIGS. 13A-13E, the stack may be placed on top of a sheet of tape (pressure-sensitive adhesive film) with a hole cut in it that is axially aligned with the center of the bellows. This tape may be first applied to a substrate, such as glass, to provide support for the structure during fabrication. The tape may allow easy removal of the bellows from the supporting substrate. Other methods may be substituted. The outer edge of the sheets may then be reinforced by applying PDMS prepolymer followed by curing to set the polymer. This process may adhere the sheets together as a permanent structure. Other adhesive methods may be used to join the sheets together.

The stacked mold may then be cut in half to allow mold separation after the molding process, but kept together. Although a mold release layer is not used here, changing the combination of mold and molding material may require the application of a thin mold release layer prior to molding.

Polyethyleneglycol (PEG) is a waxy material that may be melted (~80° C.) and then poured into the mold. PEG comes in different molecular weights which may allow easy adjustment of the stiffness of the mold produced. During the pouring process, air bubbles may get trapped in the mold and produce undesirable cavities. The bubbles may be removed while the PEG is still molten by applying a vacuum. PEG is one example of a molding material; other polymers may instead be used as the molding material.

Once the PEG is cooled and set, the PDMS mold may be carefully peeled away from the PEG structure. The PEG mold may then coated with a thin film polymer such as but not limited to Parylene C. For a PEG mold, a polymer that can be applied at room temperature or below may be used. Other mold materials may be necessary if the polymer is to be coated at higher temperatures.

Then, the Parylene coated PEG structure may be removed from the substrate by peeling the supporting pressure-sensitive adhesive film away. The film, in this example, may include a pre-cut hole to allow access to the PEG mold. If this is not present, then a hole may be made or the film may simply be removed. The Parylene coated PEG structure may then be placed in warm de-ionized water (~80° C.) to dissolve away the PEG. Finally, the tape may be separated from the final Parylene bellows structure, if necessary.

Figures 16A, 16B, 16C:
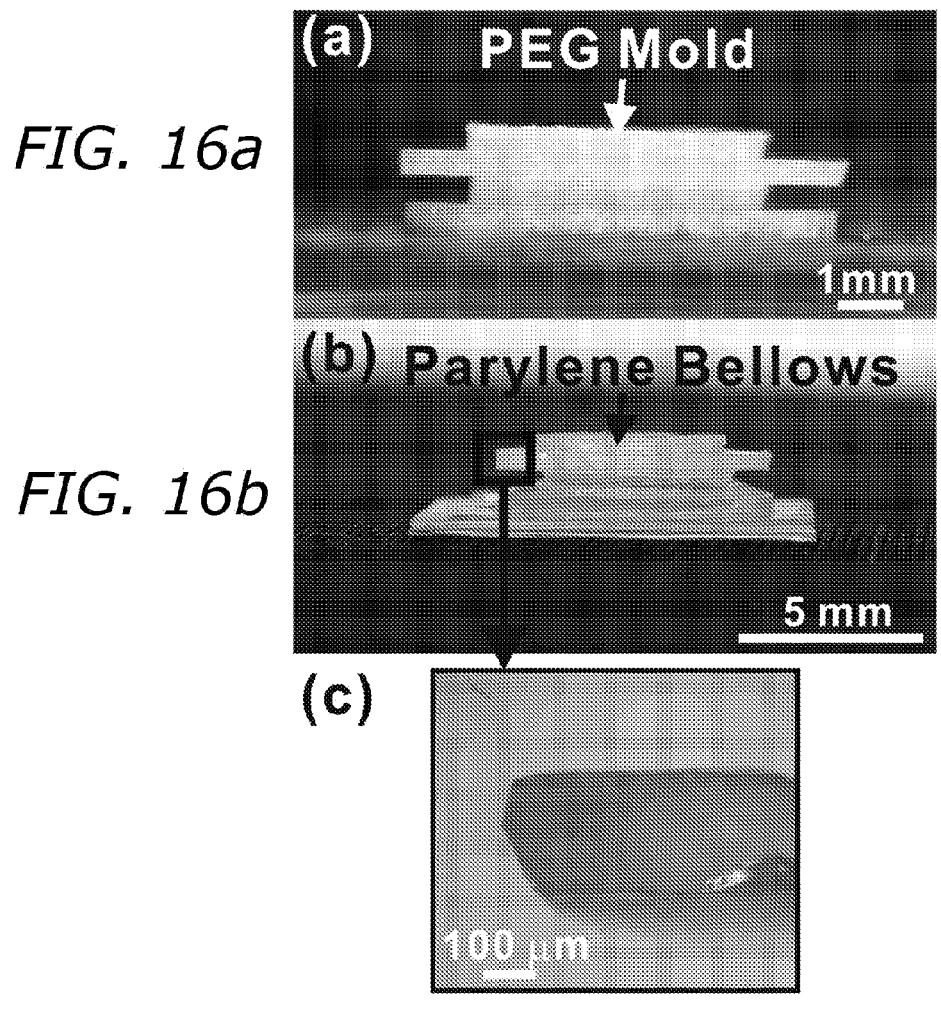
FIGS. 16A-16C are photographs of a micro-bellows mold and a micro-molded Parylene bellows produced by it.

FIGS. 16A-16C are photographs of a micro-bellows mold and a micro-molded Parylene bellows produced by it. FIG. 16A is a photograph of a PEG bellows mold; FIG. 16B is a photograph of a molded Parylene bellows that may be made from this mold; and FIG. 16C is a magnified photograph of the cross-sectional view of the top convolution of the molded bellows.

As indicated, the bellows may be fabricated using Parylene. They may instead be fabricated with other polymers or even metals. In changing the material, the fabrication process for creating the bellows structure may follow a technique similar to the one presented here or may be modified based on the material being used.

The pump base and bellows membrane may be assembled with a laser-cut, double-sided, pressure-sensitive adhesive to complete the electrolysis actuator.

Figure 17A:
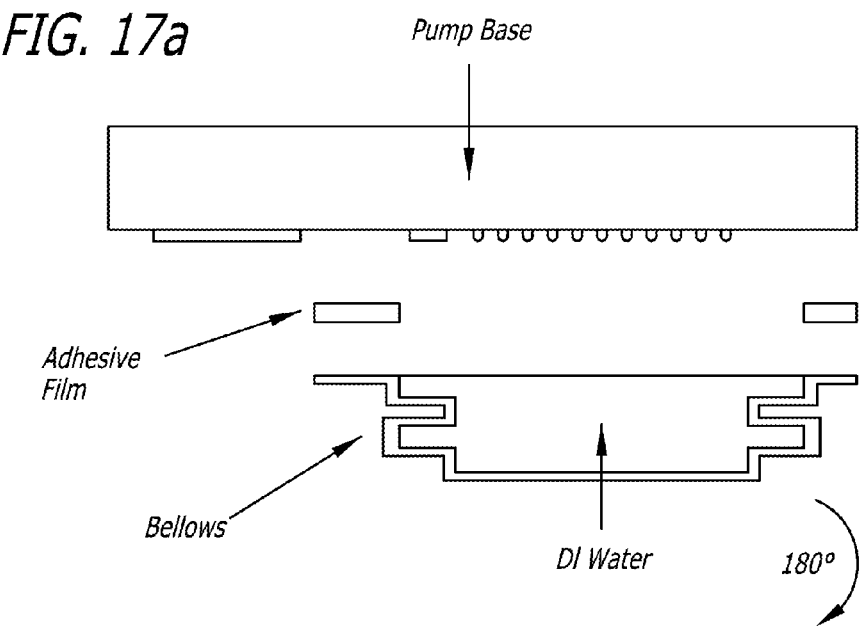
FIGS. 17A and 17B illustrate a pump actuator.
Figure 17B:
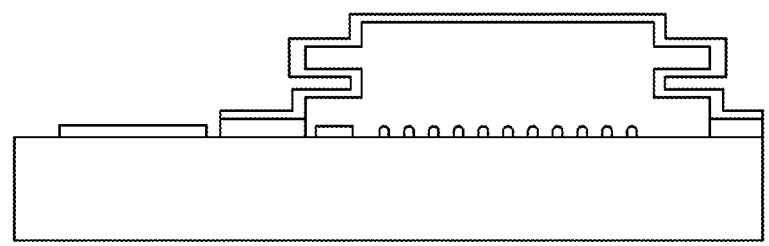

FIGS. 17A and 17B illustrate a pump actuator. FIG. 17A illustrates an exploded view of the components. FIG. 17B illustrates the assembled actuator. Constant current of about 1 mA was applied for 20 minutes. The bellows were observed to inflate uniformly to 1.5 mm.

FIGS. 18A-18C are photographs of pump actuation. FIG. 18A is a photograph of an assembled pump; FIG. 18B is a photograph of a side view of the assembled pump before constant current is applied; and FIG. 18C is a photograph of a side view of the assembled pump which shows 1.5 mm deflection after applying constant current (1 mA for 20 min).

Figure 19A:
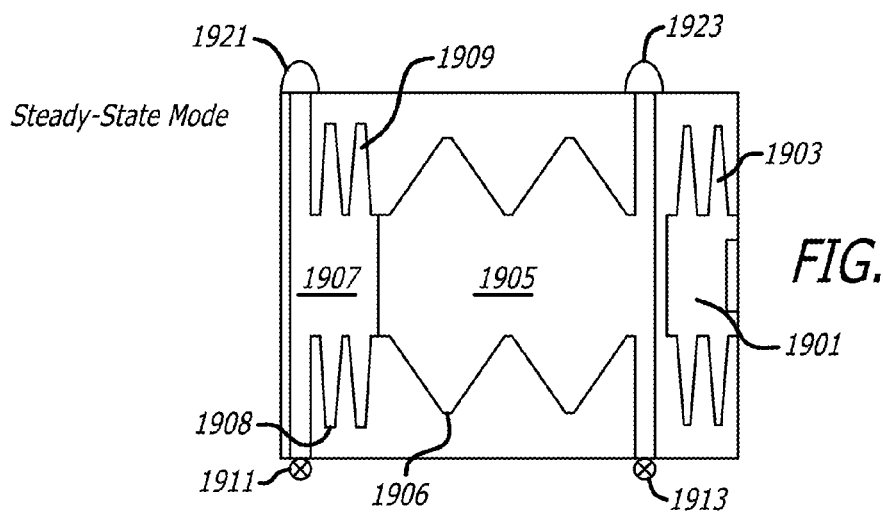
FIGS. 19A-19C illustrate operation of a simplified three-reservoir system with two one-way check valves (delivery & sampling) and two ports (refill & sampling).
Figure 19B:
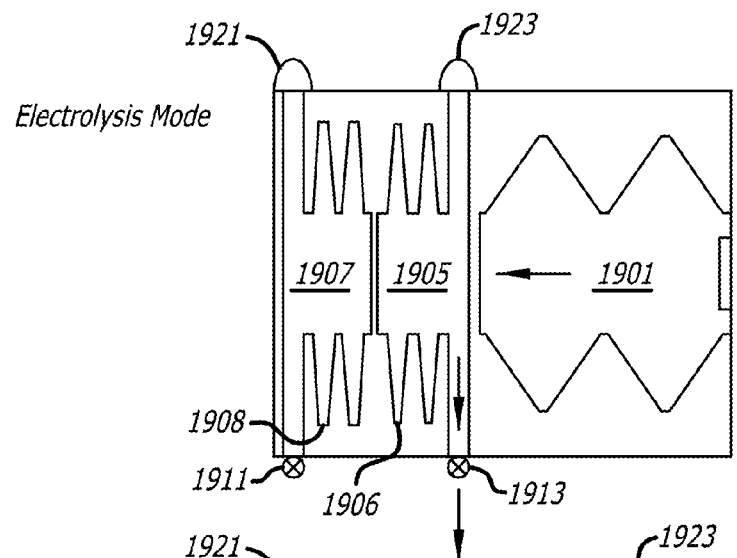
Figure 19C:
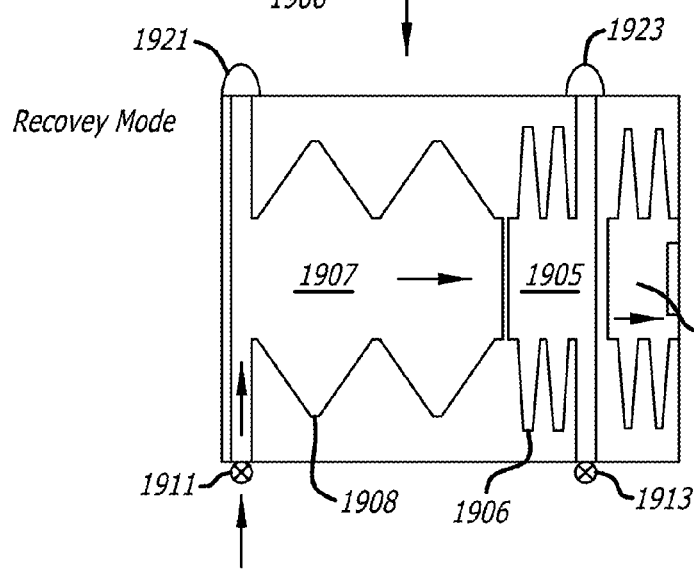

FIGS. 19A-19C illustrate operation of a simplified three-reservoir system with two one-way check valves (delivery & sampling) and two ports (refill & sampling). FIG. 19A illustrates a stead-state mode; FIG. 19B illustrates an electrolysis mode; and FIG. 19C illustrates a recovery mode.

As illustrated in these figures, bellows membranes may separate three different reservoirs, electrolysis, fluid dispensing, and sampling. When the device is "OFF" and in its "steady-state" mode (FIG. 19A), an electrolysis reservoir 1901 may be pre-filled with fluid compatible with electrolysis (e.g., water). Its associated electrolysis bellows 1903 may surround the reservoir 1901 and may be at its most collapsed state.

A fluid dispensing reservoir 1905 may be pre-filled with fluid that is to be dispensed. This may be done either prior to surgical implantation of the device or after it has been positioned in a living host. In both cases, a refill port may be used to fill its contents. A sampling reservoir 1907 may be pre-filled a small quantity of biocompatible fluid (e.g., saline). An associated sampling bellows diaphragm 1909 may be at its most collapsed state. A check valve 1911 associated with the sampling reservoir 1907 and a check valve 1913 associated with the dispensing reservoir 1905 may be in a normally closed position, preventing any fluid exchange with the external environment.

When the device is turned "ON" and in its "electrolysis" mode (FIG. 19B), within the electrolysis reservoir 1901, current may be applied to the electrolysis electrodes and the liquid may be electrolyzed into its component gas state. Because the resulting gas may take up more volumetric space, pressure $P_E$ may build up and cause the electrolysis bellows to expand and apply pressure to the other reservoirs. Within the sampling reservoir 1907, pressure $P_S$ may build up and push against the associated check valve 1911, but the check valve 1911 may not open. Within the fluid dispensing reservoir 1905, pressure $P_D$ may build up until it exceeds the 'cracking' pressure of the check valve 1913. The check valve 1913 may open allowing fluid to exit the device. The dispensing bellows 1906 may contract as fluid is expelled.

When the device is turned "OFF" and in its "recovery" mode (FIG. 19C), within the electrolysis reservoir 1901, no current may be applied and the component gases may recombine at a rate greater than the electrolysis rate, resulting in a reduction in pressure $P_E$. This shrinking volume may force the electrolysis bellows 1903 to contract. Within the fluid dispensing reservoir 1905, pressure $P_D$ may reduce until it falls below the 'cracking' pressure of check valve 1913. The check valve 1913 may close preventing any fluid exchange. Within the sampling reservoir, pressure $P_S$ may reduce until it exceeds the 'cracking' pressure of the check valve 1911. The check valve 1911 may open, allowing external fluid to enter the sampling reservoir. The increasing volume may expand the sampling bellows 1908. The device may reset to its "steady-state" mode (FIG. 19A) once available gases in the electrolysis reservoir 1901 have recombined, the bellows have equilibrated the pressures of the different reservoirs, and all check valves have closed.

While the device is in its "steady-state" mode, the dispensed fluid may either be refilled or changed with additional fluid(s) while the sampling fluid may be removed using syringes.

During the "refill/sample" mode, a coupled-dual needle syringe system may puncture a sample port 1921 and refill port 1923 simultaneously. While applying pressure on the refill needle to inject fluid via the refill port 1923 into the fluid dispensing reservoir 1905 (causing the dispensing bellows to expand), reciprocal force can be applied to the sampling needle to withdraw fluid via the sample port 1921 (causing the sampling bellows to contract)

The device may be in a different orientation and/or configuration to that which is shown in FIGS. 19A-19C. The size, shape, and scale of the structures are also not limited to that which is shown in FIGS. 19A-19C.

Figure 20A:
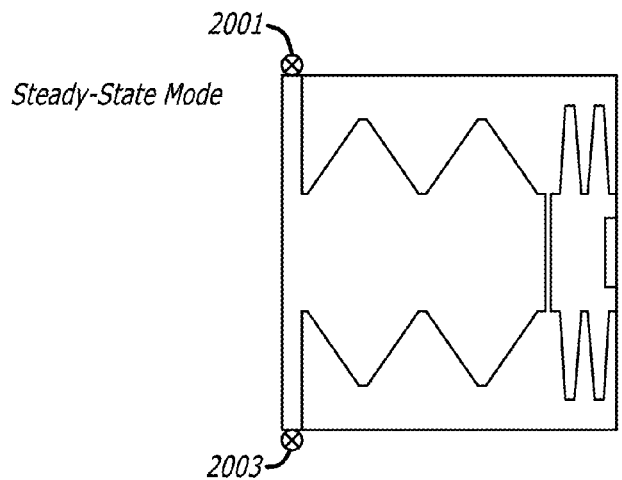
FIGS. 20A-20C illustrate an alternate configuration of a picopiston using one-way check valves and associated flexible bellows diaphragms.
Figure 20B:
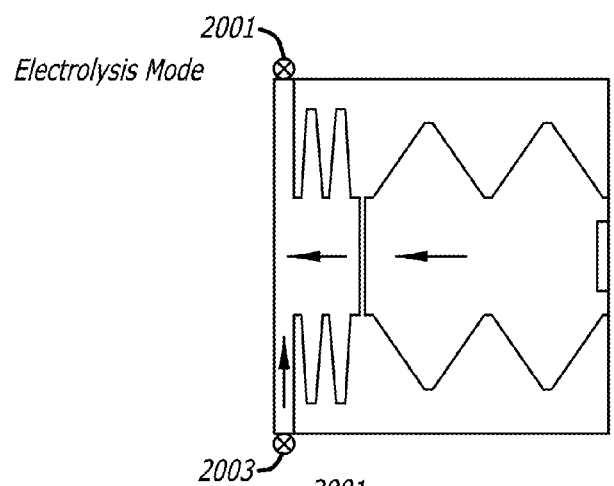
Figure 20C:
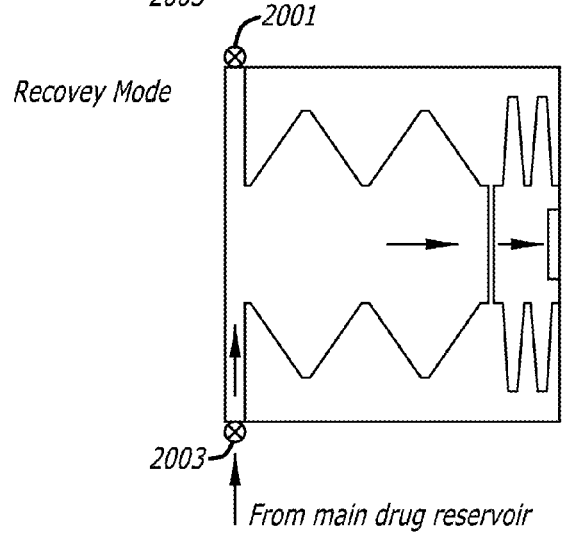

FIGS. 20A-20C illustrate an alternate configuration of a picopiston using one-way check valves 2001 and 2003 and associated flexible bellows diaphragms. FIG. 20A illustrates the device in a steady-state mode; FIG. 20B illustrates the device in an electrolysis mode; and FIG. 20C illustrates the device in a recovery mode.

Figure 21:
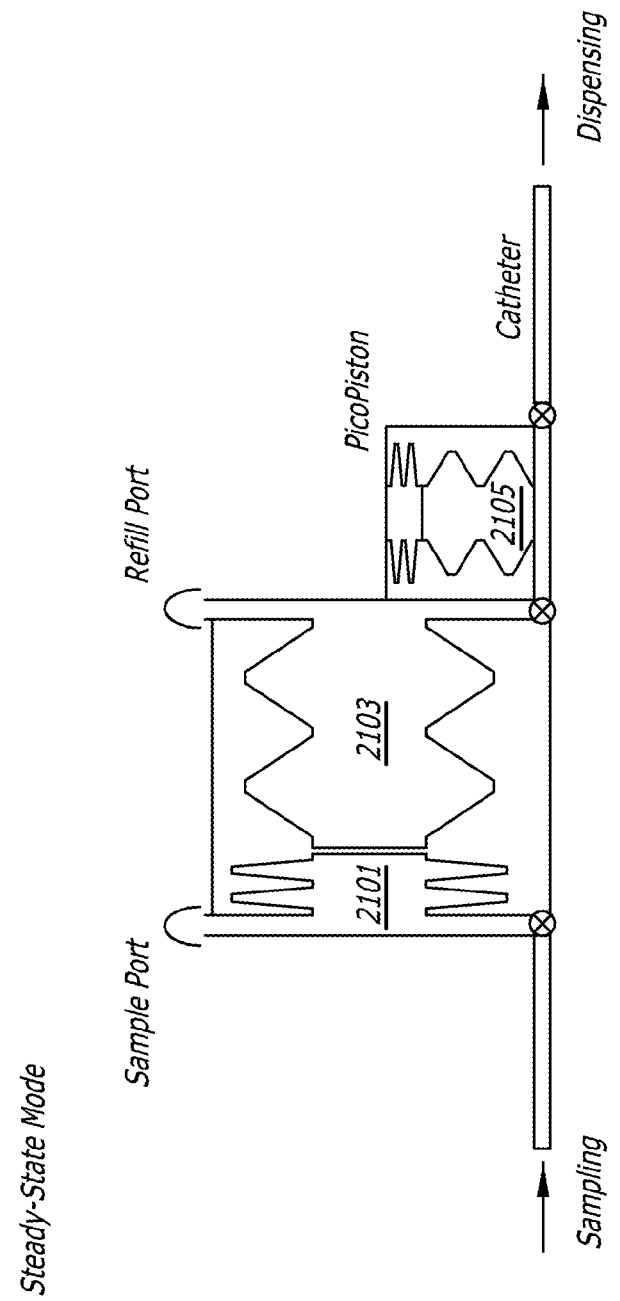
FIG. 21 illustrates an example of a system that integrates a picopiston to drive differential pressure gradients.

FIG. 21 illustrates an example of a system that integrates a picopiston to drive differential pressure gradients. The basic operating principle of this type of configured system may be similar to that described earlier. The only difference may be having two coupled dispensing reservoirs. When the electrolysis actuation is on, the bellows associated with the electrolysis reservoir may expand and may exert force on the bellows associated with a dispensing reservoir 2105. The internal pressure in the dispensing reservoir 2105 may build up and exceed the cracking pressure of the one-way valve attached to the catheter, the valve may open allowing fluid to flow out of the device. When the gas recombination rate exceeds the electrolysis rate, the electrolysis bellows may collapse, the bellows for dispensing reservoir 2105 may expand, and the catheter check valve may close. Next, the differential pressure across the one-way check valve between the two dispensing reservoirs may cause that valve to open allowing dispensing fluid from a dispensing reservoir 2103 to refill dispensing reservoir 2105. In turn, as fluid leaves dispensing reservoir 2103, its associated bellows may collapse resulting in the expansion of the coupled bellows associated with a sampling reservoir 2101. The drop in pressure in the sampling reservoir may open the one way check valve to allow external fluid to flow into the device.

The drug delivery system may be size-scalable, may have controllable fluid dispensing rates (and/or sampling rate), and may be used in a wide range of applications, including disease research in animal models as small as a mouse for scientific and/or drug discovery, study and treatment of diseases in small organs like the human eye, and the treatment of chronic conditions of a living host. The system may include a size-scalable bellows structure microfabricated with a molding process using biocompatible materials. The bellows diaphragms may separate the electrolyte from one or more fluids and may provide large deflection with low material stress.

The design and fabrication process of the microelectrodes may be optimized for power-efficient electrolysis and increased durability.

One or more one-way check valves may be employed at strategic locations in the device to regulate fluid flow. Use of one-way check valves and reservoirs may enable dispensing and sampling mechanisms to be coupled. This may address the problems of gas recombination after electrolysis and dynamic volume change of dispensing fluid reservoir throughout the device's life cycle.

One or more integrated septum access ports may allow access to the various fluid reservoirs for simultaneous refill/sample procedure.

The flexible, 3D bellows-like structure may expand with a large deflection compare to other geometries, e.g., corrugated. It may have convolutions with a polygon cross-section which in their collapsed state may be substantially perpendicular to the direction of expansion. Each convolution may have a height while collapsed in a resting and unexpanded state of no more than 1 mm. Each convolution may have a width of no more than 8 mm.

The bellow-like structure may be used to separate different fluid compartments, including the electrolyte. During operation, the bellows may expand and contract with the majority of force being focused along a single axis.

The membrane molding process may use primarily biocompatible materials. The flexible bellows structure may be microfabricated using biocompatible materials throughout the molding process. The negative mold may be made of biocompatible and/or biodegradable materials, such as polyethylene glycol (PEG). This material may have low toxicity. The material used to coat the negative mold and form the final bellows structure may be made of a flexible polymer such as Parylene C. The negative mold may then be hydrolyzed with low-temperature water avoiding any deformation of the bellows membrane. Parylene C (Specialty Coating Systems, Inc., Indianapolis, Ind.) may have good mechanical strength, biocompatibility, and ease of integration. Any USP Class VI material suitable for the construction of implants may be used as a MEMS material.

The Pt electrode fabrication process may be optimized. A series of electrode dimensions may obtain pump efficiency of close to 80%. The microfabrication process may achieve low operation temperature, since a low applied current (~$\mu$A to ~mA) and high pump efficiency may result in temperature increase for the water electrolysis reaction in the current actuator of less than 1° C. The power requirement of the current actuator may be lowered to within a few tens of nW to a few mW depending on the applied current (~$\mu$A to ~mA), so that the entire device may be powered by an implantable battery or inductively-coupled power. The electroplating process may increase surface area and result in further increased gains in efficiency.

One-way check valve(s) may be deployed at strategic locations in the device to regulate fluid flow. A one-way check valve designed to only allow flow out of the device may be strategically placed at the exiting orifice of the device or catheter. This may prevent the dispensing fluid from uncontrollable diffusing out of the device. Under conditions of high back pressure from the external fluid of a living host, the one-way valve may still not open. The valve may only open when adequate pressure is built up internally from the electrolysis reaction to exceed the 'cracking' pressure of the check valve. One-way valves purposefully placed between different reservoirs can regulate the flow between them as well, such as the picopiston operation illustrated in FIG. 21.

Check valves and reservoirs may be coupled to dispensing and sampling mechanism to address gas recombination and dynamic volume of dispensing reservoir throughout the life cycle of the device.

Septum access ports may provide access to reservoirs for the exchange of fluid(s).

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

For example, the components need not be integrated into a single device, but could be modular and located remotely from one another. For example, the bellows actuator and fluid reservoir need not be adjacent—only pneumatically coupled—for proper fluid dispensing.

Unless otherwise stated, all measurements, values, ratings, positions, magnitudes, sizes, and other specifications which are set forth in this specification, including in the claims which follow, are approximate, not exact. They are intended to have a reasonable range which is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials which have been described and their equivalents. Similarly, the phrase "step for" when used in a claim is intended to and should be interpreted to embrace the corresponding acts which have been described and their equivalents. The absence of these phrases in a claim mean that the claim is not intended to and should not be interpreted to be limited to any of the corresponding structures, materials, or acts or to their equivalents.

Nothing which has been stated or illustrated is intended or should be interpreted to cause a dedication of any component, step, feature, object, benefit, advantage, or equivalent to the public, regardless of whether it is recited in the claims.

The scope of protection is limited solely by the claims which now follow. That scope is intended and should be interpreted to be as broad as is consistent with the ordinary meaning of the language which is used in the claims when interpreted in light of this specification and the prosecution history which follows and to encompass all structural and functional equivalents.

The invention claimed is:

1. An implantable fluid delivery system comprising:
    a fluid reservoir configured to hold a supply of fluid, to dispense that fluid under the control of an actuator, and adapted to be implanted within the body of a living host; and
    an actuator within the fluid reservoir configured to cause the fluid to be controllably dispensed from the fluid reservoir, the actuator including:
        a bellows configured to expand in a direction when inflated, the bellows having folds with surfaces which run substantially perpendicular to the direction of expansion in a collapsed state and which define a stacked set of convolutions, each of which has a collapsed height of no more than 1 mm, the stacked set of convolutions being stacked in their collapsed state in substantially the direction of expansion; and
        electrodes configured to come in electrical contact with an electrolyte within the bellows and to cause electricity to run through the electrolyte, thereby causing the electrolyte to break down into a gas and, in turn, to cause the bellows to expand in the direction of expansion.

2. The implantable fluid delivery system of claim 1 wherein the implantable fluid delivery system is adapted to be fit within a human eye.

3. The implantable fluid delivery system of claim 1 wherein the implantable fluid delivery system is configured such that the fluid and the electrolyte cannot mix.

4. The implantable fluid delivery system of claim 3 wherein the actuator creates a sealed chamber from which electrolyte cannot leak.

5. The implantable fluid delivery system of claim 1 wherein the stacked set of convolutions in the bellows taper in width.

6. The implantable fluid delivery system of claim 1 wherein the bellows are made of a thin film polymer.

7. The implantable fluid delivery system of claim 1, wherein each of the folds has a width perpendicular to the direction of expansion of no more than 8 mm.

8. The implantable fluid delivery system of claim 6 wherein the thin film polymer is Parylene C.

* * * * *